(12) United States Patent
Petrikovics et al.

(10) Patent No.: US 9,456,996 B2
(45) Date of Patent: Oct. 4, 2016

(54) FORMULATIONS OF DIMETHYL TRISULFIDE FOR USE AS A CYANIDE ANTIDOTE

(71) Applicant: Sam Houston State University, Huntsville, TX (US)

(72) Inventors: Ilona Petrikovics, Huntsville, TX (US); Kristof I. Kovacs, Huntsville, TX (US)

(73) Assignee: Sam Houston State University, Huntsville, TX (US)

( * ) Notice: Subject to any disclaimer, the term of this patent is extended or adjusted under 35 U.S.C. 154(b) by 0 days.

(21) Appl. No.: 14/685,014

(22) Filed: Apr. 13, 2015

(65) Prior Publication Data

US 2015/0297535 A1     Oct. 22, 2015

Related U.S. Application Data

(60) Provisional application No. 61/978,504, filed on Apr. 11, 2014.

(51) Int. Cl.

| | | |
|---|---|---|
| A61K 31/105 | (2006.01) |
| A61K 47/40 | (2006.01) |
| A61K 47/20 | (2006.01) |
| A61K 47/02 | (2006.01) |
| A61K 47/26 | (2006.01) |
| A61K 9/00 | (2006.01) |
| A61K 33/04 | (2006.01) |
| A61K 33/00 | (2006.01) |

(52) U.S. Cl.
CPC ........... *A61K 31/105* (2013.01); *A61K 9/0019* (2013.01); *A61K 33/00* (2013.01); *A61K 33/04* (2013.01); *A61K 47/02* (2013.01); *A61K 47/20* (2013.01); *A61K 47/26* (2013.01); *A61K 47/40* (2013.01)

(58) Field of Classification Search
None
See application file for complete search history.

(56) References Cited

U.S. PATENT DOCUMENTS

| | | |
|---|---|---|
| 4,292,311 A | 9/1981 | Sarnoff |
| 2014/0120159 A1 | 5/2014 | Petrikovics et al. |

FOREIGN PATENT DOCUMENTS

| | | | |
|---|---|---|---|
| EP | 2184100 | * 7/2008 | ............ B01F 17/00 |
| WO | 2011/133893 | 10/2011 | |

OTHER PUBLICATIONS

Tisserand et al, Essential Oil Safety, 2014, Churchill Livingstone, 2nd edition, p. 291.*
Cardiofy Website—www.cardiofy.com/plant_phytochemistry.htm, downloaded Jul. 17, 2012.
Zottola et al. "Disulfides as Cyanide Antidotes: Evidence for a New in Vivo Oxidative Pathway for Cyanide Detoxification" Chem. Res. Toxicol. 2009, 22, 1948-1953.
Bhattacharya "Antidotes to Cyanide Poisoning: Present Status" Indian Journal of Pharmacology 2000; 32: 94-101.

(Continued)

*Primary Examiner* — Trevor Love
(74) *Attorney, Agent, or Firm* — Meyertons, Hood, Kivlin, Kowert & Goetzel, P.C.; Eric B. Meyertons

(57) ABSTRACT

Dimethyl trisulfide antidote compositions may be used to as a cyanide poisoning antidote. Formulations of dimethyl trisulfide may be made in an aqueous solvent system that includes water and one or more of a co-solvent, a surfactant, a cyclodextrin, and a phospholipid.

9 Claims, 16 Drawing Sheets

(56) References Cited

OTHER PUBLICATIONS

Iciek et al. "Allyl disulfide as donor and cyanide as acceptor of sulfane sulfur in the mouse tissues" Pharmacology Report 57, 212-218.

Frankenberg et al. "Enzyme therapy in cyanide poisoning: Effect of rhodanese and sulfur compounds" Archives of Toxicology, Oct. 1980, vol. 45, Issue 4, pp. 315-323.

Petrikovics Developement and Efficacy Testing of Next Generation Cyanide Antidotes, Annual Report for US Army Medical Research and Material Command, Award No. w81XWH-12-2-0126, pp. 1-85, Oct. 2013.

Kovacs "Identification, Solubility Enhancement and in vivo Testing of a Cyanide Antidote Candidate" European Journal of Pharmaceutical Sciences, (2013), 49, 352-358.

International Search Report / Written Opinion for PCT Application No. PCT/US2015/025525 issued Jul. 8, 2015.

International Search Report / Written Opinion for PCT Application No. PCT/US2015/025528 issued Jul. 8, 2015.

Mnayer et al. entitled "Chemical Composition, Antibacterial and Antioxidant Activities of Six Essential Oils from the Alliaceae Family" Molecules 2014, 19, 20034-20053.

* cited by examiner

FORMULATIONS OF DIMETHYL TRISULFIDE FOR USE AS A CYANIDE ANTIDOTE

PRIORITY CLAIM

This application claims priority to U.S. Provisional Application Ser. No. 61/978,504 entitled "FORMULATIONS OF DIMETHYLTRISULFIDE FOR USE AS A CYANIDE ANTIDOTE" filed Apr. 11, 2014, which is incorporated herein by reference in its entirety.

BACKGROUND

1. Field of the Invention

The present invention relates to antidotes for blood agents. More particularly, the invention relates to cyanide antidotes.

2. Brief Description of the Related Art

Cyanide (CN) intoxication in humans can occur in a number of scenarios including as part of a chemical weapon-based military conflict. CN causes rapid and extensive cellular hypoxia through the binding of the ferric ($Fe^{3+}$) iron in the cytochrome c oxidase system leading to the collapse of the electron transport chain and thereby inhibiting the efficiency of oxygen transport to the tissues. Common cyanide compounds include hydrogen cyanide gas, cyanogen chloride gas, and crystalline solids such as potassium cyanide and sodium cyanide. The ease of delivery of these agents (especially gaseous cyanides) allow them to be used as an attack agent in chemical warfare.

Therapeutic attempts to counteract cyanide poisoning have been developed to inhibit the toxic effects of cyanide. For example, oxygen, sodium thiosulfate, amyl nitrite, sodium nitrite, 4-dimethylaminophenol, hydroxocobalamin, dicobalt EDTA, garlic extracts, disulfides, sodium pyruvate, alpha-keto-glutaric acid, aqueous solutions of ferrous sulfate in a citric acid sodium carbonate solution have been for cyanide detoxification.

Presently in the United States two kits have been accepted as the standard of care. One is based on the intravenous administration of a combination of sodium nitrite (SN) and sodium thiosulfate (TS) (Nithiodote®), while the other intravenously used preparation contains hydroxocobalamin (Cyanokit®). Hydroxocobalamin binds to CN and forms cyanocobalamin, which is then excreted in the urine. Sodium nitrite leads to the formation of methemoglobin which has high affinity to CN and forms a relative stable complex of cyanomethemoglobin. Acting as a sulfur donor, TS helps bolster the natural CN detoxification by endogenous sulfur transferases, such as rhodanese (Rh), which utilize sulfur and convert CN into thiocyanate.

U.S. Pat. No. 4,565,311 to Samoff, which is incorporated herein by reference, describes as an antidote for cyanide poisoning injectable hydroxylamine hydrochloride. This is followed by treatment with thiosulfate. The hydroxylamine hydrochloride can also be employed as a respiratory stimulant in treating other illnesses.

Zottola et al. in "Disulfides as Cyanide Antidotes: Evidence for a New In Vivo Oxidative Pathway for Cyanide Detoxification." Chemical Research Toxicology, 2009, 22, pp. 1948-1953, which is incorporated herein by reference, describes the conversion of cyanide to thiocyanate in the presence of the enzyme rhodanese. Rhodanese is an enzyme found primarily in the mitochondria mainly of the liver and kidney. In a mammal, rhodanese is thought to be responsible for the conversion of cyanide to thiocyanate (SCN). Thiocyanate is then excreted by the kidney. Oxidized sulfur species such as sodium thiosulfate have been shown to be effective in vitro donors for rhodanese, however sodium thiosulfate in vivo efficacy is highly limited due to its limited cell penetration capability to reach the endogenous rhodanese. Thus, more effective sulfur analogs are desired.

The present therapies of sodium thiosulfate (TS) and sodium nitrite (SN) (Nithiodote), and the hydroxocobalamin (Cyanokit) both have limitations of requiring intravenous administration. Additionally, TS is highly dependent on the presence of sulfurtransferase enzyme (Rhodanese), and cannot easily penetrate through the mitochondrial membrane to reach the endogenous Rhodanese. The Cyanokit requires high volume of administration to reach the required dose. There is, therefore, a need to develop a new, fast acting cyanide antidote, that can be administered in a way that provides rapid absorption to protect individuals without requiring specialized techniques such as intravenous injection.

SUMMARY

Cyanide antidote methods are described herein. In some embodiments, a method of treating cyanide intoxication in a subject, comprises administrating to a subject who would benefit from such treatment a therapeutically effective amount of dimethyl trisulfide (DMTS). The dimethyl trisulfide may be administered as a solution subcutaneously or intramuscularly.

A pharmaceutical composition for treating cyanide intoxication in a subject, includes DMTS formulated in a solvent system, such as co-solvent and/or a surfactant. These formulation methods are used to make the lipid soluble DMTS water soluble, making it appropriate for subcutaneous or intramuscular administration. In another embodiment, lipid based micelles may also be applicable for subcutaneous or intramuscular administration.

In an embodiment, the solvent system may be composed of water and a co-solvent. The co-solvent may be an alcohol (e.g., ethanol, polyethylene glycol, etc.) or an ether (e.g., polyethylene glycol (PEG)).

In an embodiment, the solvent system may be composed of water and a surfactant (e.g., cholate, deoxycholate, cremophore, polysorbate). The surfactant may be a non-ionic surfactant (e.g., ethoxylated castor oil). In some embodiments, a cyclodextrin may be used to improve the water solubility of DMTS.

In an embodiment, the solvent system comprises water, a surfactant, and a co-solvent.

In an embodiment, a method of treating cyanide intoxication in a subject, includes administrating to a subject who would benefit from such treatment a therapeutically effective amount of a pharmaceutical composition comprising DMTS solubilized in an aqueous solvent system, wherein the aqueous solvent system comprises: water, a co-solvent and/or a surfactant. The DMTS pharmaceutical composition may be administered subcutaneously, intramuscularly, transdermally, intraosseously, or using an aerosol delivery system, or via other commonly accepted means of administration.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which.

Figure 1:
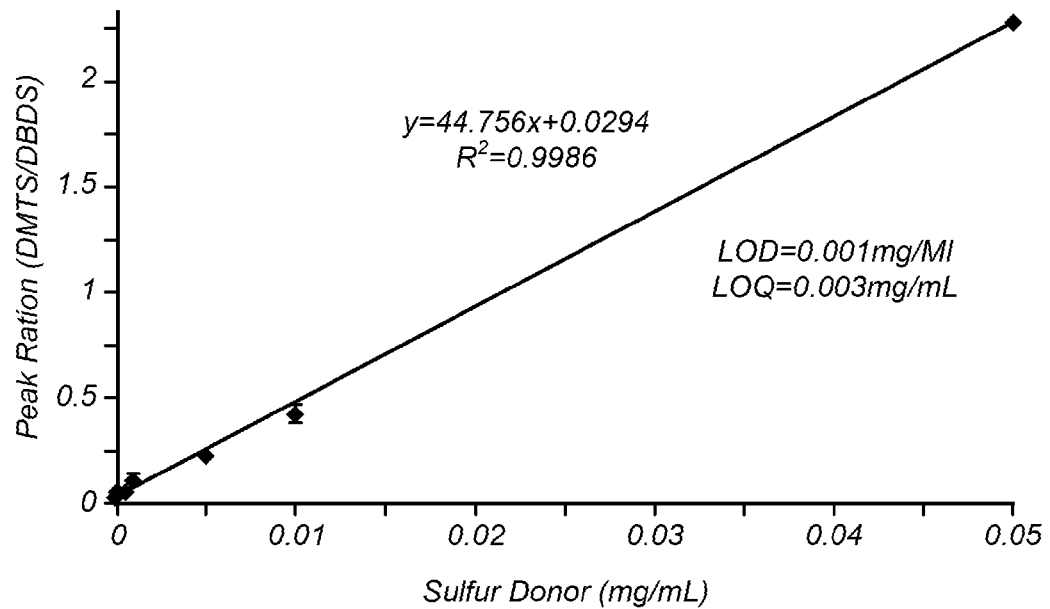
FIG. 1 depicts a GC/MS calibration curve used to determine the concentration of DMTS in a solvent system.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION

It is to be understood that the present embodiments are not limited to particular compounds, methods or biological systems, which may, of course, vary. It is also to be understood that, as used in this specification and the appended claims, the singular forms "a", "an", and "the" include singular and plural referents unless the content clearly dictates otherwise. It is to be yet further understood that any terminology used herein is for the purpose of describing particular embodiments only, and is not intended to be limiting.

The terms used throughout this specification generally have their ordinary meanings in the art, within the context of the invention, and in the specific context where each term is used. Certain terms are discussed below or elsewhere in the specification, to provide additional guidance to the practitioner in describing the general embodiments of the invention, as well as how to make and use them. It will be readily appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

As used herein, phrases such as "one or more additional compositions or medicaments suitable for the treatment of the toxic effects of cyanide in a subject," or more simply, "one or more additional compositions or medicaments," generally refer to a pharmaceutical composition that contains at least one pharmaceutically active compound that is used for the treatment of the toxic effects of cyanide in a subject, but which is distinct from the sulfur analogs or derivatives that form the basis of the present disclosure.

As used herein "cyanide intoxication" is to be understood to mean a medical condition that is characterized by cyanide interference with the performance of the cytochrome oxidase system thereby inhibiting the efficiency of oxygen transport to the tissues.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein the terms "administration," "administering," or the like, when used in the context of providing a pharmaceutical or nutraceutical composition to a subject generally refers to providing to the subject one or more pharmaceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, intraosseous, transdermal, or buccal routes of delivery. Alternatively, or concurrently, administration may be by the oral route. The dosage administered will be dependent upon the age, health, weight, and/or intoxicated state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

As used herein the terms "subject" generally refers to a mammal, and in particular to a human.

The terms "in need of treatment," "in need thereof," "who would benefit from such treatment," or the like when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal has been exposed to cyanide and that may be detoxified, ameliorated, or treated with the specified medical intervention.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the mammalian host treated and the particular mode of administration.

The term "pharmacologically inert," as used herein, generally refers to a compound, additive, binder, vehicle, and the like, that is substantially free of any pharmacologic or "drug-like" activity.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

A method of treating cyanide intoxication in a subject includes administering to a subject who would benefit from such treatment a therapeutically effective amount of dimethyl trisulfide (DMTS). DMTS is a pale yellow clear oily liquid with a melting point of 58° C. at 15 mmHg. It is insoluble in aqueous solvents (solubility=0.13 mg/ml in distilled water) but soluble in most organic solvents. It is widely distributed in nature and is used as an FDA approved food flavoring/fragrance agent in food industry. The amount of DMTS administered is sufficient to convert at least some cyanide ions in the subject to SCN. The SCN may be excreted by the subject's kidney system.

DMTS, exhibits inadequate aqueous solubility making the formulation of liquid dosage forms of DMTS difficult. In some embodiments, the low aqueous solubility of DMTS may be resolved by dissolving DMTS in a pharmaceutically acceptable solvent system or carrier. In the case of DMTS, specifically it is desirable to utilize a solvent system that increase the concentration of DMTS, since the aqueous solubility of DMTS is 0.13 mg/ml. If a solvent system was not used, and water was used as the only solvent, the volume of injection to be administered, if a therapeutically active dose is provided, would generally exceed the tolerable limit. Thus a composition comprising a solvent system with a higher DMTS concentration would allow for a smaller injection volume which would make the use of DMTS for the treatment of cyanide intoxication feasible.

In one embodiment an aqueous solution having DMTS in therapeutically effective amounts may be formed in a solvent system that includes water and an alcohol. In some embodiments, a solvent system may include water and a surfactant. In some embodiments, a solvent system may include water, an alcohol, and a surfactant.

In compositions where the therapeutically effective amount of pharmaceutically active ingredient cannot be dissolved in water alone, adequate amounts of solubilizing excipients such as co-solvents or surfactants can be used. It is well known for one skilled in the arts that the amount of organic or non-aqueous solvents or excipients, replacing water in the composition in a dosage form, especially in parenteral (intramuscular) dosage forms, is limited due to the toxicity of these excipients. It is generally accepted to apply as little non-aqueous excipients as possible.

Co-solvents are pharmaceutically acceptable excipients added to water to solubilize poorly water soluble molecules. They exert their solubility by: 1) decreasing the dielectric constant of the solvent system and 2) disrupting the secondary bonding structure of water. In an embodiment, co-solvents include, but are not limited to, alcohols and ethers. Alcohols that may be used include alkyl alcohols (e.g., methanol, ethanol, propanol, etc.) and polyols (e.g., propylene glycol, glycerol, etc.). Ethers that may be used include, but are not limited to, polyethylene glycols. Examples of polyethylene glycols that may be used in a solvent system include, but are not limited to: PEG 200; PEG 300; and PEG 400. It should be understood that the list is merely illustrative and any analog or derivate or a mixture of the stated molecules are included within the scope of the present invention.

Surfactants are pharmaceutically acceptable excipients added to water above a certain concentration, the so called critical micellar concentration to form micelles. These micelles form mainly in aqueous media and they are responsible for increasing the solubility of poorly water soluble drugs, such as DMTS. In one embodiment, surfactants are amphiphylic molecules belonging to the group of ionic or non-ionic surfactants. Examples of non-ionic surfactants that may be used to improve the solubility of DMTS include, but are not limited to polysorbates and ethoxylated castor oil (Cremophor®). It should be understood that the list is merely illustrative and any analog or derivate or a mixture of the stated molecules are included within the scope of the present invention.

Cyclodextrins may also be used to improve the solubility of DMTS in water. Cyclodextrins are pharmaceutically acceptable excipients added to water to increase the solubility of poorly water soluble drugs. Cyclodextrins form inclusion complexes with the poorly soluble drugs thus increasing the water solubility. In one embodiment cyclodextrins that may be used include, but not limited to, alpha-, beta- and gamma cyclodextrins and their derivatives. It should be understood that the list is merely illustrative and any analog or derivate or a mixture of the stated molecules are included within the scope of the present invention.

In an embodiment, a solvent system capable of delivering a therapeutic amount of DMTS to a subject is composed of a mixture of water and a cyclodextrin. In an embodiment, the concentration of cyclodextrin in water may range from about 1% to about 50% by weight. Exemplary cyclodextrins that may be dissolved in water to form a solvent system include, but are not limited to: β (beta)-cyclodextrin; γ (gamma)-cyclodextrin; randomly methylated β (beta)-cyclodextrin; and hydroxypropyl β (beta)-cyclodextrin. Specific water based solvent systems that may be used to dissolve a therapeutic amount of DMTS include, but are not limited to: 1-50% β (beta)-cyclodextrin in water; 1-50% γ (gamma)-cyclodextrin in water; 1-50% randomly methylated β (beta)-cyclodextrin in water; and 1-50% hydroxypropyl β(beta)-cyclodextrin in water.

In an embodiment, a solvent system capable of delivering a therapeutic amount of DMTS to a subject is composed of a mixture of water and a co-solvent. The co-solvent may be an alcohol or an ether. In an embodiment, the concentration of alcohol and/or ether in water may range from about 1% to about 80%, or from 10% to 75% by weight. Exemplary alcohols and ethers that may be dissolved in water to form a solvent system include, but are not limited to: PEG 200; PEG 300; PEG 400; propylene glycol; and ethanol. Specific water based solvent systems that may be used to dissolve a therapeutic amount of DMTS include, but are not limited to: 25-75% PEG 200 in water; 25-75% PEG 200:propylene glycol (1:1) in water; 25-75% propylene glycol in water; 25-75% PEG 300 in water; 25-75% PEG 300:propylene glycol (1:1) in water; 25-75% PEG 200:PEG 300 (1:1) in water; 25-75% propylene glycol:ethanol (1:1) in water; 25-75% PEG 200:ethanol (1:1) in water; 25-75% ethanol in water; and 25-75% PEG 300:ethanol (1:1) in water.

In an embodiment, a solvent system capable of delivering a therapeutic amount of DMTS to a subject is composed of a mixture of water and a surfactant. In some embodiments, the solvent system is composed of water and a non-ionic surfactant. In an embodiment, the concentration of surfactant in water may range from about 1% to about 50%, or from 5% to 20% by weight. Exemplary non-ionic surfactants that may be dissolved in water to form a solvent system include, but are not limited to: polysorbates and ethoxylated castor oil (Cremophor® RH40 and Cremophor® EL). Exemplary polysorbates include, but are not limited to, Polysorbate 20, Polysorbate 40, Polysorbate 60 and Polysorbate 80. Specific water based solvent systems that may be used to dissolve a therapeutic amount of DMTS include, but are not limited to: 1-50% Cremophor® RH 40 in water; 1-50% Cremophor® EL in water; 1-50% Polysorbate 80: Cremophor® RH 40 (1:1) in water; 1-50% Cremophor® EL:Cremophor® RH 40 in water; 1-50% Polysorbate 80: Cremophor® EL (1:1) in water; and 1-50% Polysorbate 80 in water.

In an embodiment, a solvent system capable of delivering a therapeutic amount of DMTS to a subject is composed of a mixture of water, a surfactant, and a co-solvent. In some embodiments, the solvent system is composed of water, a non-ionic surfactant, and an alcohol and/or ether. In an embodiment, the concentration of surfactant in water may range from about 1% to about 25%, or from 5% to 20% by weight. The concentration of co-solvent may range from about 1% to about 80%, or from 10% to 75% by weight. Specific water based solvent systems that may be used to dissolve a therapeutic amount of DMTS include, but are not limited to: 1-20% hydroxypropyl β (beta)-cyclodextrin:10-50% PEG 400 in water; 1-20% Polysorbate 80:1-75% ethanol in water; 1-20% Cremophor® EL:1-75% ethanol in water; and 1-20% Cremophor® EL:1-75% PEG 200 in water.

As noted above, the solvent system for the administration of DMTS for the treatment of cyanide toxicity should be chosen to maximize the concentration of DMTS in the solvent system, while minimizing the amount of additives used to increase the solubility of the DMTS. In one embodiment, an optimized solvent system for the delivery of DMTS is composed of 15-20% Polysorbate 80 in water.

Micelles represent and offer an attractive avenue to developing a carrier system for the lipophilic DMTS molecule. Micelles are spherical structures composed of a hydrophobic core and a hydrophilic corona with sizes ranging from 5-50 nm. They may be produced by hydrating films of block co-polymers like PEG-PE. Instead of forming bilayers and subsequent liposomes, the unique structure of block co-polymers allow them to partition into a hydrophobic phase consisting of the fatty acid tails of the phospholipids surrounded by the hydrophilic groups consisting of the PEG and phosphate groups. Pegylated micelles have been proposed and used as carriers of hydrophobic anticancer drugs like paclitaxel.

In one embodiment, micelles may be formed which encapsulate DMTS, allowing DMTS to be dispersed in an aqueous solvent system. Micelles containing DMTS may be formed by using a phospholipid. Phospholipids, as used herein, are natural or synthetic molecules that include a diglyceride and a phosphate containing group coupled to the diglyceride. Phospholipids that may be used to form micelles for delivery of DMTS to subjects have the general structure:

where:
$R^1$ is $C_{13}$-$C_{21}$ alkyl or $C_{13}$-$C_{21}$ alkenyl (monounsaturated or polyunsaturated);
X is 5-120; and
$R^2$ is hydroxyl, alkyl ether, azide, or $NH_2$.

Exemplary phospholipids that may be used to form micelles for the delivery of DMTS to subjects include, but are not limited to: 1,2-dimyristoyl-sn-glycero-3-phosphoethanolamine-N-[methoxy(polyethylene glycol)-350] (ammonium salt); 1,2-dipalmitoyl-sn-glycero-3-phosphoethanolamine-N-[methoxy(polyethylene glycol)-350] (ammonium salt); 1,2-distearoyl-sn-glycero-3-phosphoethanolamine-N-[methoxy(polyethylene glycol)-350] (ammonium salt); 1,2-dioleoyl-sn-glycero-3-phosphoethanolamine-N-[methoxy(polyethylene glycol)-350] (ammonium salt); 1,2-dimyristoyl-sn-glycero-3-phosphoethanolamine-N-[methoxy(polyethylene glycol)-550] (ammonium salt); 1,2-dipalmitoyl-sn-glycero-3-phosphoethanolamine-N-[methoxy(polyethylene glycol)-550] (ammonium salt); 1,2-distearoyl-sn-glycero-3-phosphoethanolamine-N-[methoxy(polyethylene glycol)-550] (ammonium salt); 1,2-dioleoyl-sn-glycero-3-phosphoethanolamine-N-[methoxy(polyethylene glycol)-550] (ammonium salt); 1,2-dimyristoyl-sn-glycero-3-phosphoethanolamine-N-[methoxy(polyethylene glycol)-750] (ammonium salt); 1,2-dipalmitoyl-sn-glycero-3-phosphoethanolamine-N-[methoxy(polyethylene glycol)-750] (ammonium salt); 1,2-distearoyl-sn-glycero-3-phosphoethanolamine-N-[methoxy(polyethylene glycol)-750] (ammonium salt); 1,2-dioleoyl-sn-glycero-3-phosphoethanolamine-N-[methoxy(polyethylene glycol)-750] (ammonium salt); 1,2-dimyristoyl-sn-glycero-3-phosphoethanolamine-N-[methoxy(polyethylene glycol)-1000] (ammonium salt); 1,2-dipalmitoyl-sn-glycero-3-phosphoethanolamine-N-[methoxy(polyethylene glycol)-1000] (ammonium salt); 1,2-distearoyl-sn-glycero-3-phosphoethanolamine-N-[methoxy(polyethylene glycol)-1000] (ammonium salt); 1,2-dioleoyl-sn-glycero-3-phosphoethanolamine-N-[methoxy(polyethylene glycol)-1000] (ammonium salt); 1,2-dimyristoyl-sn-glycero-3-phosphoethanolamine-N-[methoxy(polyethylene glycol)-2000] (ammonium salt); 1,2-dipalmitoyl-sn-glycero-3-phosphoethanolamine-N-[methoxy(polyethylene glycol)-2000] (ammonium salt); 1,2-distearoyl-sn-glycero-3-phosphoethanolamine-N-[methoxy(polyethylene glycol)-2000] (ammonium salt); 1,2-dioleoyl-sn-glycero-3-phosphoethanolamine-N-[methoxy(polyethylene glycol)-2000] (ammonium salt); 1,2-dimyristoyl-sn-glycero-3-phosphoethanolamine-N-[methoxy(polyethylene glycol)-3000] (ammonium salt); 1,2-dipalmitoyl-sn-glycero-3-phosphoethanolamine-N-[methoxy(polyethylene glycol)-3000] (ammonium salt); 1,2-distearoyl-sn-glycero-3-phosphoethanolamine-N-[methoxy(polyethylene glycol)-3000] (ammonium salt); 1,2-dioleoyl-sn-glycero-3-phosphoethanolamine-N-[methoxy(polyethylene glycol)-3000] (ammonium salt); 1,2-dimyristoyl-sn-glycero-3-phosphoethanolamine-N-[methoxy(polyethylene glycol)-5000] (ammonium salt); 1,2-dipalmitoyl-sn-glycero-3-phosphoethanolamine-N-[methoxy(polyethylene glycol)-5000] (ammonium salt); 1,2-distearoyl-sn-glycero-3-phosphoethanolamine-N-[methoxy(polyethylene glycol)-5000] (ammonium salt); 1,2-dioleoyl-sn-glycero-3-phosphoethanolamine-N-[methoxy(polyethylene glycol)-5000] (ammonium salt); 1,2-distearoyl-sn-glycero-3-phosphoethanolamine-N-[azido(polyethylene glycol)-2000] (ammonium salt); 1,2-distearoyl-sn-glycero-3-phosphoethanolamine-N-[succinyl(polyethylene glycol)-2000] (ammonium salt); 1,2-distearoyl-sn-glycero-3-phosphoethanolamine-N-[carboxy(polyethylene glycol)-2000] (ammonium salt); 1,2-distearoyl-sn-glycero-3-phosphoethanolamine-N-[maleimide(polyethylene glycol)-2000] (ammonium salt); 1,2-distearoyl-sn-glycero-3-phosphoethanolamine-N-[PDP(polyethylene glycol)-2000] (ammonium salt); 1,2-distearoyl-sn-glycero-3-phosphoethanolamine-N-[amino(polyethylene glycol)-2000] (ammonium salt); 1,2-distearoyl-sn-glycero-3-phosphoethanolamine-N-[biotinyl(polyethylene glycol)-2000] (ammonium salt); 1,2-distearoyl-sn-glycero-3-phosphoethanolamine-N-[cyanur(polyethylene glycol)-2000] (ammonium salt); 1,2-distearoyl-sn-glycero-3-phosphoethanolamine-N-[folate(polyethylene glycol)-2000] (ammonium salt); and 1,2-distearoyl-sn-glycero-3-phosphoethanolamine-N-[folate(polyethylene glycol)-5000] (ammonium salt).

Micelles may be formed by the optimized process set forth below. The phospholipid, in most instances may be commercially obtained in powder form or as a solution in a suitable solvent (e.g., chloroform). In the case of the phospholipid being in powder form, the phospholipid is dissolved/suspended in ethanol. If obtained as a solution in chloroform, the chloroform and dissolved in ethanol. The ethanol is then removed (e.g., by evaporation) to form a lipid film. The lipid film is hydrated with water to form phospholipid micelles. Excess DMTS is added to the hydrated phospholipid composition. The mixture of DMTS and micelles was subjected to ultrasound or vortex mixing for a time sufficient to create a composition of micelles of DMTS dispersed in water.

One or more of the additional compounds suitable for the treatment of the cyanide intoxication presently contemplated may be formulated as a separate pharmaceutical composition to be administered in conjunction with the subject sulfur analogs as part of a therapeutic regimen, or may be formulated in a single preparation together with the sulfur analog. A combined composition may be administered orally, parenterally, by inhalation spray, rectally, intraosseously (IO), subcutaneously, sublingually, or topically or in an eye drop form in dosage unit formulations containing conventional nontoxic pharmaceutically acceptable carriers, adjuvants, and vehicles as desired. Topical administration may involve the use of transdermal administration such as transdermal patches or iontophoresis devices. The term parenteral generally embraces non-oral routes of administration, including but not limited to, subcutaneous injections, intravenous, intramuscular, intrasternal injection, or infusion techniques.

Cyanide poisoning can cause death quickly in the victims that ingest or inhale substances that produce systemic cyanide poisoning in the victim. Death from cyanide poisoning can occur in less than 24 hours, generally 2-6 hours depending how the cyanide was administered. For the treatment of cyanide poisoning it is therefore important to be able to administer an effect detoxification agent quickly. Most commercially available cyanide poisoning treatments are designed for intravenous injection. While intravenous injection allows rapid delivery of the detoxification agent, it requires a skilled person to administer properly. Since cyanide poisoning is generally associated with warfare or terrorist attacks it is important to have an administration method that is suitable for a large untrained population. Intramuscular or subcutaneous administration would achieve this goal, since the injection site would not be critical. In some embodiments, the injection may be administered into the muscle of the patient (i.e., intramuscular injection). In another embodiment, DMTS may be administered by subcutaneous injection.

Therapeutic kits that include DMTS are also contemplated herein. Such kits will generally contain, in a suitable container, a pharmaceutically acceptable formulation of DMTS. The kits also may contain other pharmaceutically acceptable formulations, such as those containing components to target the DMTS to distinct regions of a patient where treatment is needed, as well as appropriate devices for delivery of the dimethyl sulfide to the subject (e.g., an injection device).

The kits may have a single container that contains the DMTS, with or without any additional compositions or medicaments, or they may have distinct container means for each desired composition. The container of the kit will generally include at least one vial, test tube, flask, bottle, syringe or other container, into which the DMTS, and any other desired agent, may be placed and, preferably, suitably aliquoted. Where additional components are included, the kit will also generally contain a second vial or other container into which these are placed, enabling the administration of separated designed doses. The kits also may comprise a second/third container means for containing a sterile, pharmaceutically acceptable buffer or other diluent/excipient.

The kits also may contain a device to administer the pharmaceutical compositions to an animal or patient, e.g., one or more needles or syringes, or even an eye dropper, pipette, or other such like apparatus, from which the formulation may be injected into the animal or human. The kits may also include a means for containing the vials, or such like, and other component, in close confinement for commercial sale, such as, e.g., injection or blow-molded plastic containers into which the desired vials and other apparatus are placed and retained.

Non-limiting examples of DMTS efficacy and formulation testing are described herein.

Examples

General Example for the Solubility Tests

Each of the solutions applied in the solubilization tests were prepared as follows:
1. The required amount of co-solvent or surfactant or co-solvent and surfactant combinations, or cyclodextrin was measured by weight into a beaker or a volumetric flask and the specific amount of water was added.
2. This solvent system was then vigorously shaken until complete homogenization of the solution was achieved.
3. An excess amount of the active agent was added to the solution (excess amount was defined as more DMTS than what could be solubilized by the solvent system). (preparing a saturated solution)
4. Determine the concentration of DMTS in the saturated solution using GC-MS or HPLC.

Analytical Methods

GC-MS Analytical Method to Determine DMTS

The system consisted of an Agilent Technologies 7890A GC with a 7683 autosampler and a 5975C VL MSD, triple-Axis detector (Agilent Technologies, Santa Clara, Calif., USA). A DB-5MS column (30 m×0.25 mm ID, 0.25 µm film thickness; Agilent Technologies, Santa Clara, Calif., USA) was used with He carrier gas at a flow rate of 1 ml/min and pressure of 7.6522 psi. The conditions for GC and MS are detailed in the following tables:

TABLE 1

| Gas chromatograph parameters | |
|---|---|
| Injection Source: | GC Auto-loading sampler (ALS) |
| Injection Volume: | 1.0 µL |

TABLE 1-continued

| Gas chromatograph parameters | |
|---|---|
| Injection Port Temperature: | 250° C. |
| Injection Mode: | Split |
| Split Ratio: | 60:1 |
| Carrier Gas: | helium |
| Carrier Gas Velocity: | 1.0 ml/min |
| Carrier Gas Pressure: | 7.6522 psi |
| Initial Temperature of Column: | 50° C. |
| Initial Temperature Duration: | 2 mins |
| Temperature Ramp: | 5° C./min |
| Final Temperature of Column: | 250° C. |
| Final Temperature Duration: | 5 mins |

TABLE 2

| Mass spectrometer parameters | |
|---|---|
| EMV Mode: | Relative (+200) |
| EM Voltage: | 1118 |
| Solvent Delay: | 2.00 mins |
| Source temperature: | 230° C. |
| Quadrupole temperature: | 150° C. |
| Electron energy: | 70 eV |

The GC/MS calibration curve used to determine the concentration of DMTS in a solvent system is shown in FIG. 1.

Extraction Protocol for GC-MS Samples
1. Prepare diluted solution 1 (DS1)
   a. Take 25 µl of the formulated DMTS sample and transfer it to a microcentrifuge tube.
   b. Add 375 µl of 100% ethanol
   c. Add 100 µl of the internal standard (1 mg/mL DBDS in 100% ethanol)
   d. Vortex for 6 minutes by automated vortexer
2. Prepare diluted solution 2 (DS2)
   a. Transfer 50 µl of DS1 to another microcentrifuge tube (like in Step 1)
   b. Add 250 µl of pure cyclohexanone
   c. Vortex the solution for 6 minutes by automatic vortexer
   d. Centrifuge for 5 minute at 5000 rpm at 4° C.
3. Transfer 100 µl of the top layer of DS2 into a GC-MS vial containing an insert for small volumes.
4. Measure on GC-MS HPLC Analytical Method to Determine DMTS HPLC was performed using a ProStar HPLC system having: 2 Solvent Delivery Modules (master and servant), Model 210; AutoSampler, Model 410; UV/VIS Detector, Model 340; Fluorescence Detector, Model 363; (AutoSampler and Fluorescence Detector were not used). Stationary phase: Phenomenex Luna 5µ C8(2) 100 Å 250×4.60 mm 5 micron. Mobil phase: Water/ACN:40/60, flow rate: 1 mL/min. Injection 25 µL (loop 20 µL). UV/V is Detector Setting: 215 nm. Retention Time for DMTS: approximately 9.5 minutes.

Figure 2:
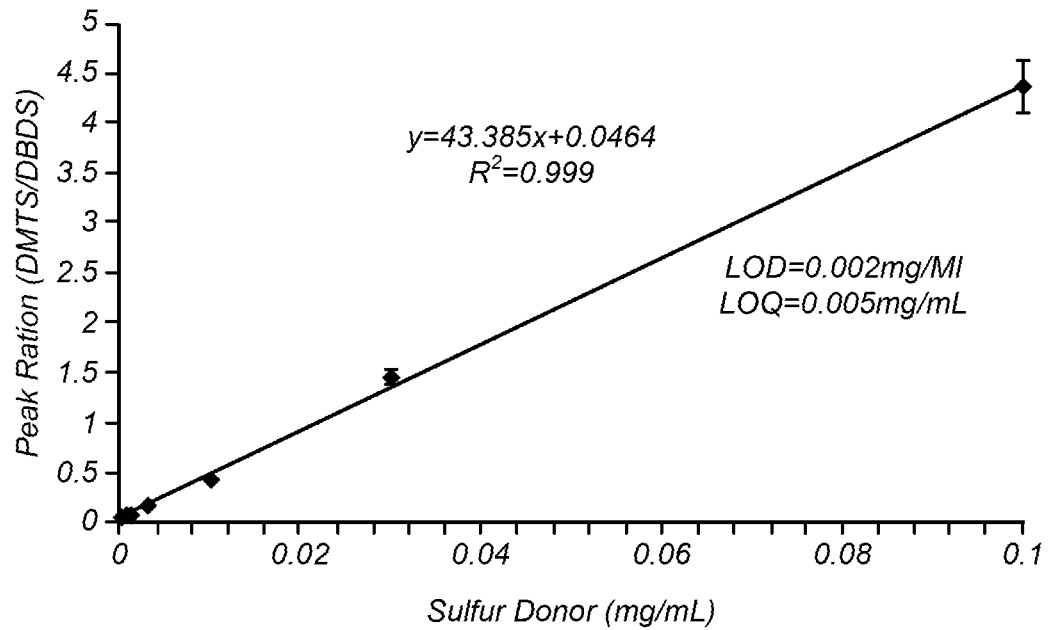
FIG. 2 depicts an HPLC calibration curve used to determine the concentration of DMTS in a solvent system.

Take 10 µL of formulation and add it to an ependorph tube containing 990 µL of ethanol. Vortex for 5 minutes then inject onto HPLC for measurement. FIG. 2 depicts an HPLC calibration curve used to determine the concentration of DMTS in a solvent system.

Solubility Tests

Figure 3:
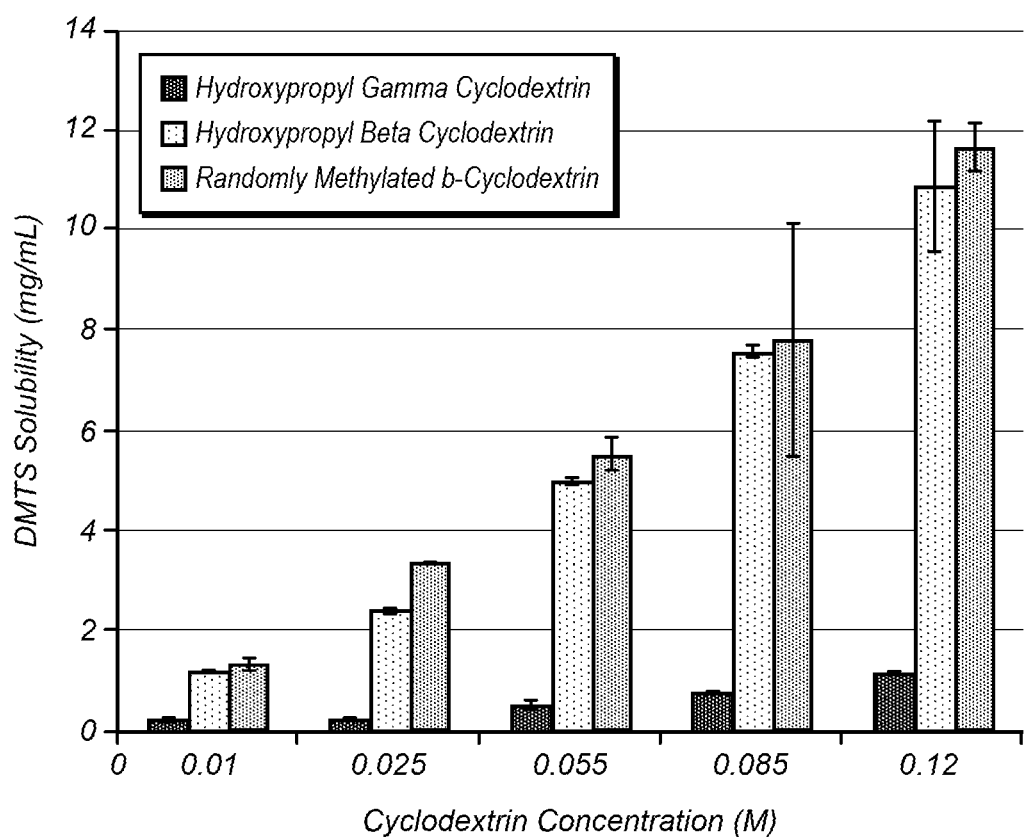
FIG. 3 depicts the solubility of DMTS in various cyclodextrin based solvent systems.
Figure 4:
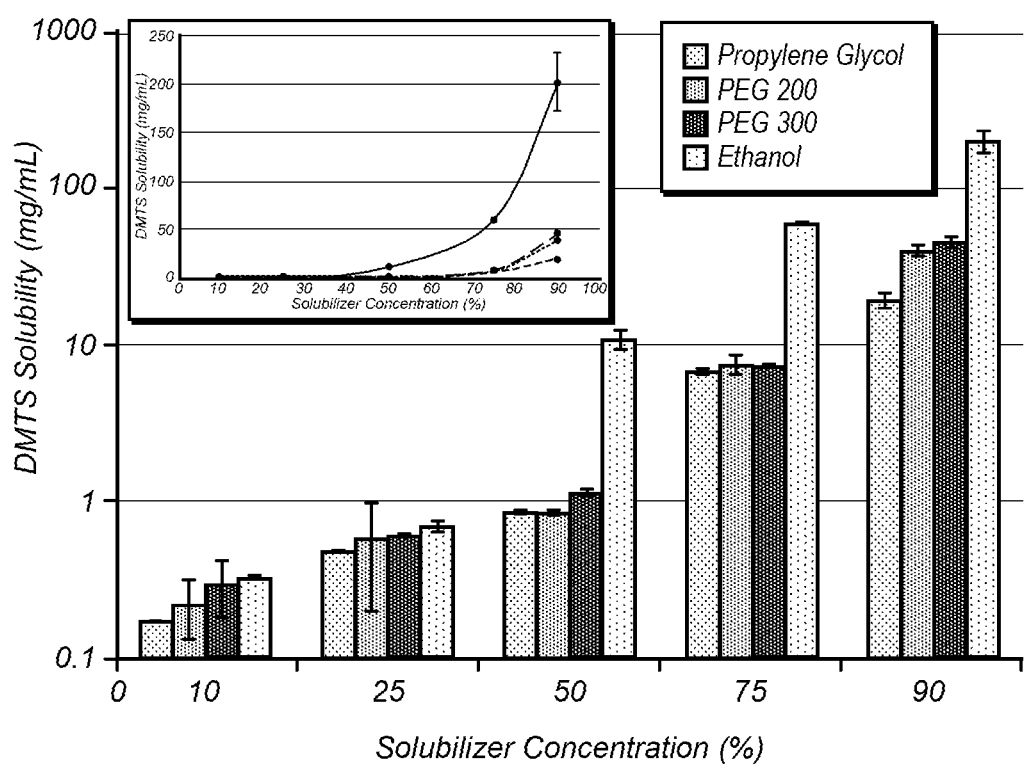
FIG. 4 depicts the solubility of DMTS in various co-solvents and combinations of co-solvents.
Figure 5:
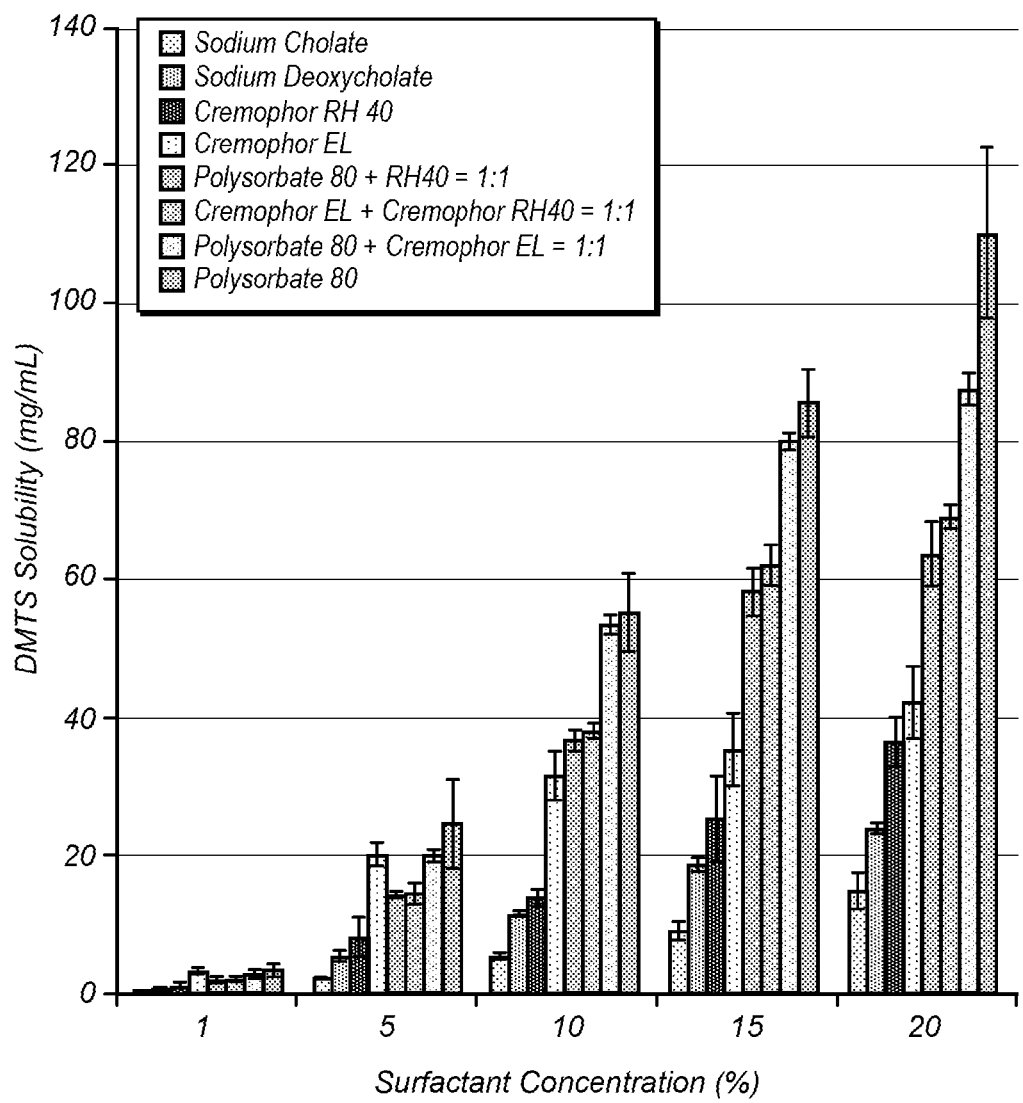
FIG. 5 depicts the solubility of DMTS in various surfactants.
Figure 6:
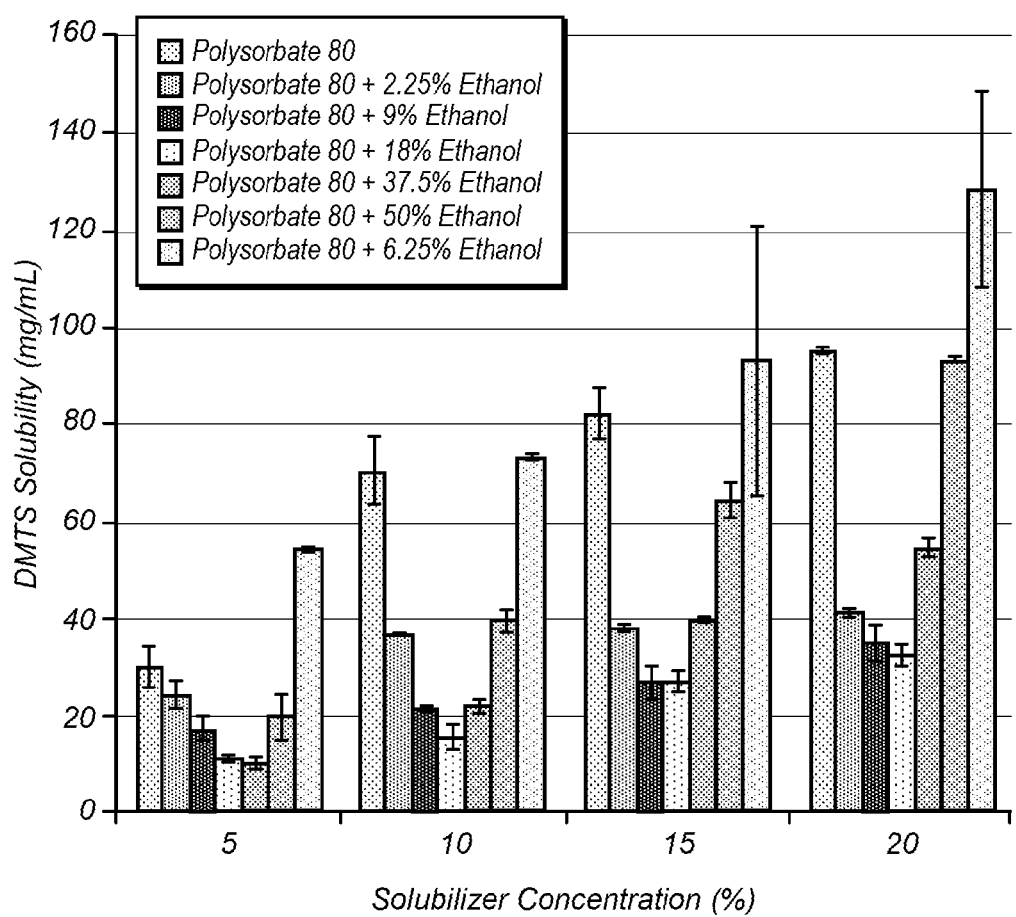
FIG. 6 depicts the solubility of DMTS in various co-solvent and surfactant combinations.
Figure 7:
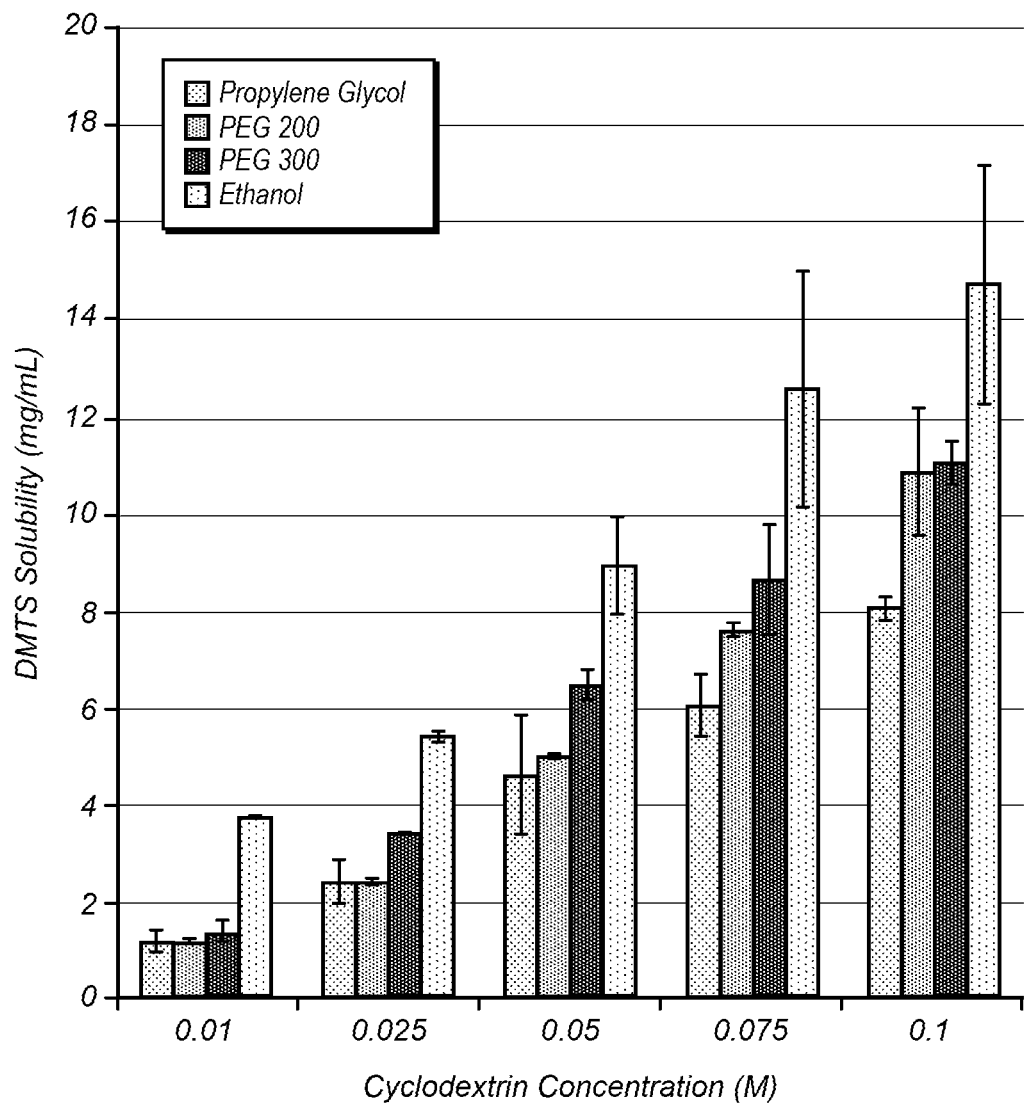
FIG. 7 depicts the solubility of DMTS in co-solvent and cyclodextrin combinations.

FIG. 3 depicts the solubility of DMTS in various cyclodextrin based solvent systems. FIG. 4 depicts the solubility of DMTS in various co-solvents and combinations of co-solvents. FIG. 5 depicts the solubility of DMTS in various surfactants and combinations of surfactants. FIG. 6 depicts the solubility of DMTS in various co-solvent and surfactant combinations. FIG. 7 depicts the solubility of DMTS in co-solvent and cyclodextrin combinations.

DMTS Determination in Blood

Figure 8:
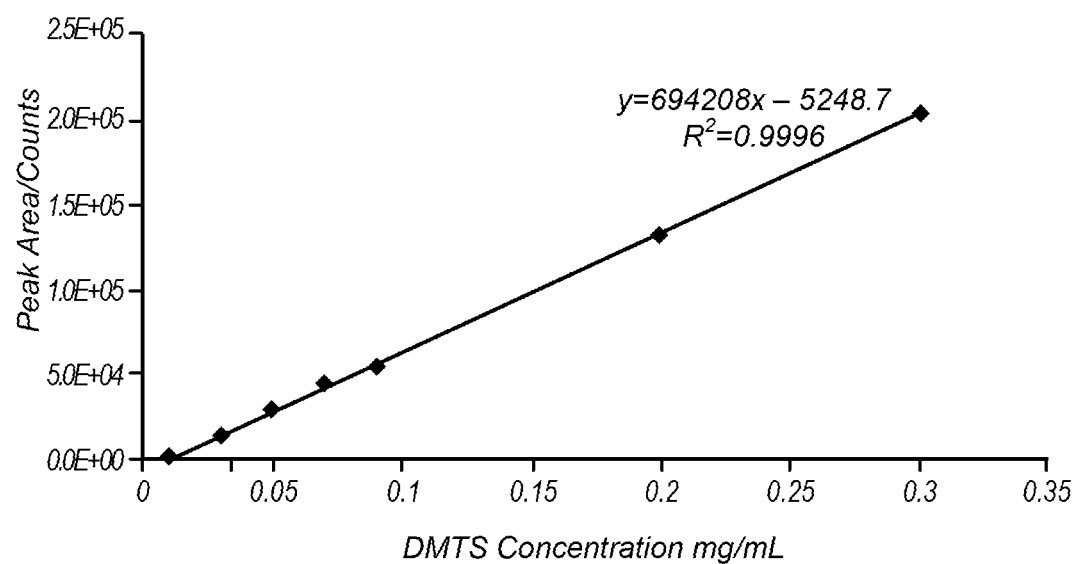
FIG. 8 depicts a calibration curve for determining DMTS in blood by HPLC.

The concentration of DMTS in blood was determined using the process developed by Thompson and SeSilva, in press). Briefly, 1200 µL of blood was drawn from a rat injected with a DMTS solution. This sample was then centrifuged at 13,500 rpm and 4° C. for 10 minutes. Once the sample was centrifuged, the top liquid layer was carefully removed with a micro pipet and discarded. The bottom layer was then sonicated for 10 minutes to break up the red blood cells. Next, 400 µL of cyclohexanone was added to the sonicated cells and the sample was vortexed for 5 minutes. It was then centrifuged with the previous settings for 10 minutes. 50 µL of the clear upper layer was then carefully drawn using a micro pipet and transferred to a clean ependorph tube and 25 µL of this was drawn and injected into the HPLC. The DMTS concentration is determined from a calibration curve. FIG. 8 depicts a calibration curve for determining DMTS in blood by HPLC.

DMTS Pharmacokinetics

Figure 9:
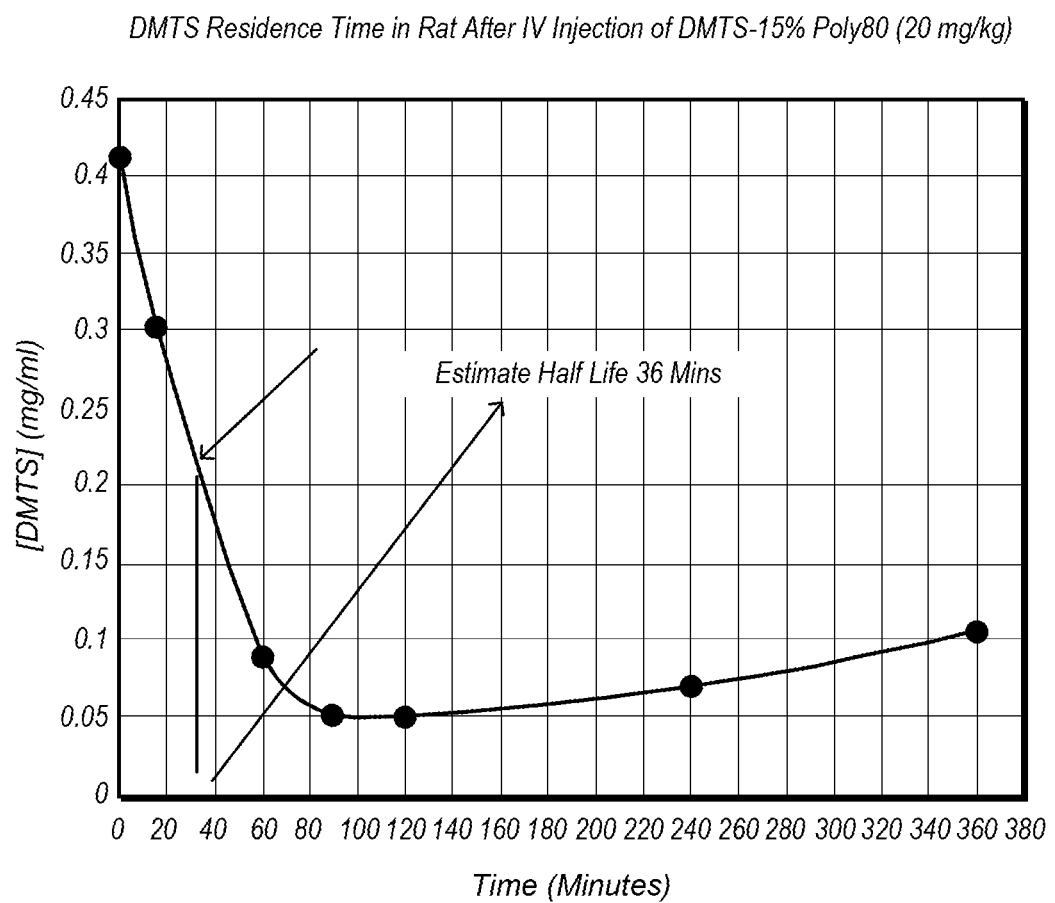
FIG. 9 depicts residence time data obtained by injecting DMTS dissolved in a solvent system composed of 15% Poly80 in water into rats.

A cyanide antidote, DMTS, was injected intravenously (IV for residence time determination), and intramuscularly (IM for absorption kinetics study) into rats in these pharmacokinetic studies. FIG. 9 depicts residence time data obtained by injecting DMTS dissolved in a solvent system composed of 15% Poly80 in water into rats. Formulated DMTS was injected intravenously (20 mg/kg), and blood samples were taken at periodic time intervals.

Absorption Kinetics with 15% Poly80-DMTS

FIG. 10 depicts absorption kinetical data obtained by injecting DMTS dissolved in a solvent system composed of 15% Poly80 in water into rats. Formulated DMTS was injected intramuscularly (250 mg/kg), and blood samples were taken at periodic time intervals.

In Vivo Antidotal Efficacy of DMTS in 15% Poly80 vs. 20% Poly80

TABLE 3

Antidotal Potency Ratios for DMTS

| Exp # | Treatments | | | APR* |
|---|---|---|---|---|
| 1 | DMTS (intramuscular) | 100 mg/kg | 15% Poly80 | 3.4 |
| 2 | DMTS (intramuscular) | 100 mg/kg | 20% Poly80 | 3.2 |

*APR = LD50 of CN with DMTS/LD50 of CN without DMTS (control)

Method for In Vivo Antidotal Efficacy Determination in a Mice Model

LD50 studies were conducted using the Dixon up-and-down method (Dixon W. 1965. The up-and-down method for small samples. Am. Stat. Assoc. 12:967-978) with 1.0 mg/ml and 3.5 mg/ml KCN solutions in (saline solution), a 50 mg/ml DMTS stock solution (in 15% polysorbate 80), and a 100 mg/ml TS solution (in water). Male CD-1 mice (Charles River Breeding Laboratories, Inc., Wilmington, Mass.) weighing 18-28 g were housed at 21° C. and in light-controlled rooms (12-h light/dark, full-spectrum lighting cycle with no twilight), and were furnished with water and 4% Rodent Chow (Teklad HSD, Inc., CITY, Wis.) ad libitum. All animal procedures were conducted in accordance with the guidelines by "The Guide for the Care and Use of Laboratory Animals" (National Academic Press, 2010), accredited by AAALAC (American Association for the Assessment and Accreditation of Laboratory Animal Care, International). At the termination of the experiments, surviving animals were euthanized in accordance with the 1986 report of the AVMA Panel of Euthansia.

Animal studies were conducted as therapeutic experiments using the Dixon up-and-down method for LD50 determination (Dixon, W. J., 1965. The up-and-down method for small animal samples. Am. Stat. Assoc. J. 12, 967-978) and the estimated 95% confidence interval was determined by the method of Bruce (Bruce R. D. 1985. An Up-and-Down procedure for acute toxicity testing. Fundam Appl Toxicol. 5:15-157). The injection volume of the subcutaneously administered KCN stock solution was calculated based on the weight of the animal and the dose of KCN applied for each stages. (The starting dose of KCN is usually determined based of the previous experiences with the given antidotes, and it is changed in the next stages accordingly to the computer's suggestion based on the result of dead or alive that is registered after each dose of KCN administration). Within 30 seconds following the KCN administration, a predetermined dose (either 25 mg/kg, 50 mg/kg, 100 mg/kg or 200 mg/kg) of DMTS (50 mg/ml in 15% polysorbate 80) alone or in combination with sodium thiosulfate/magnesium thiosulfate (TS) (100 mg/ml in water or in 15% polysorbate 80) was injected intramuscularly into the rear right leg of the mouse. (When TS was administered in water, it was administered into a separate leg to avoid the DMTS solubility issues). The mice were then inspected and determined to be alive or dead. Based on the observation, a higher or a lower dose of KCN was injected in the following stage. This was repeated until enough data was collected to determine the LD50 values, and the program declared that the stopping condition has been met. For each LD50 determination, 9-14 animals were used.

Storage Stability Studies with 15% Poly80-DMTS

Protocol

Approximately three solutions of 275 mL of 15% Polysorbate 80 was prepared. HCl was added to the first solution to bring the total pH of the 15% Polysorbate 80 solution to a pH of 6. The second solution was adjusted to a pH of 7 and the third solution was adjusted to a pH of 8 using NaOH. Next, three 50 mg/mL DMTS solutions were made in 250 mL volumetric flasks. 12.5 g of DMTS was weighed out into each volumetric flask. The three different pH 15% Polysorbate 80 solutions were added to the flasks, each flask receiving a different pH. Each flask was mixed until all of the DMTS is dissolved. 135 Snap-it vials and 135 8 mL glass vials were labeled according to their pH, the temperature in which they were stored, and the day in which they were tested. The three temperatures used in this experiment were 0° C., 20° C., and 40° C. The days are t=3 days, t=6 days, t=9 days, t=22 days, and t=31 days. The appropriate solutions were placed in the appropriate Snap-It vial as full as possible. The lid was put on and the vial placed in the appropriate 8 mL vial and the lid put on. The lids were crimped closed. The solutions were opened and measured only on the appropriate day. They were measured only once. A t=0 measurements were done from each stock solution to establish the "100%". FIG. 11 depicts stability data for 15% Poly80-DMTS at pH=7 as a function of temperature and time.

Advantages of the 15% and 20% Polysorbate 80/50 mg/Ml DMTS Composition

Preventing necrosis—There was no any tissue damage shown at the injection site on the legs after injecting 15% Poly80-DMTS up to 200 mg/kg doses. At doses over 200 mg/kg, there were visible damage on the injection sites, therefore it is not recommended to employ doses higher than 200 mg/kg, with the formulation that contains 50 mg/ml DMTS.

Figure 11A:
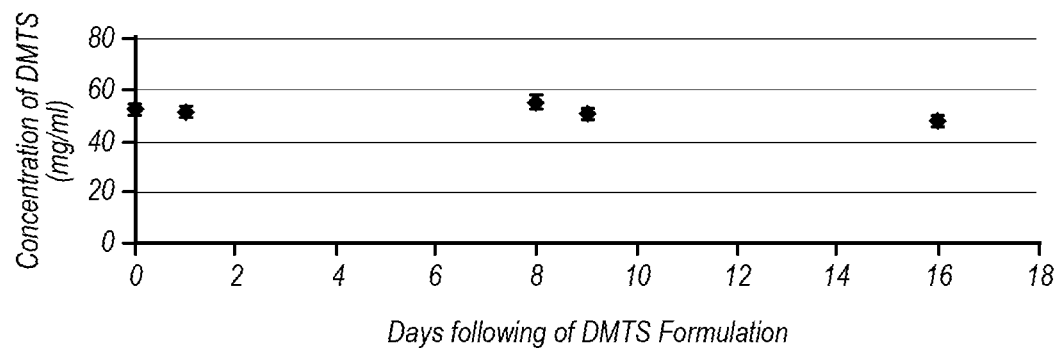
FIGS. 11A-B depict stability data for 15% Poly80-DMTS and 20% Poly80-DMTS.
Figure 11B:
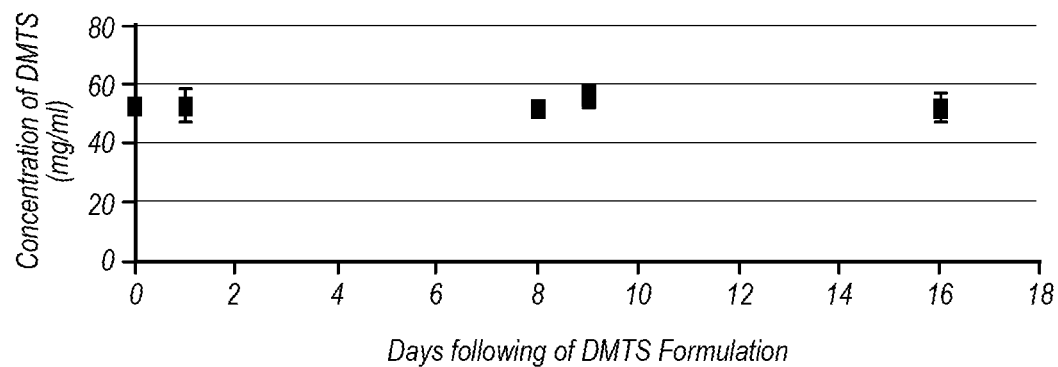
Figure 11C:
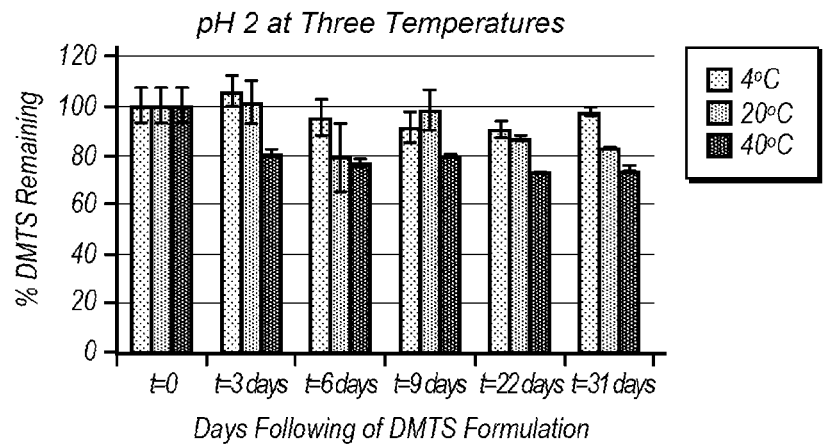
FIGS. 11C-G depicts stability data for 15% Poly80-DMTS at various pH as a function of temperature and time.
Figure 11D:
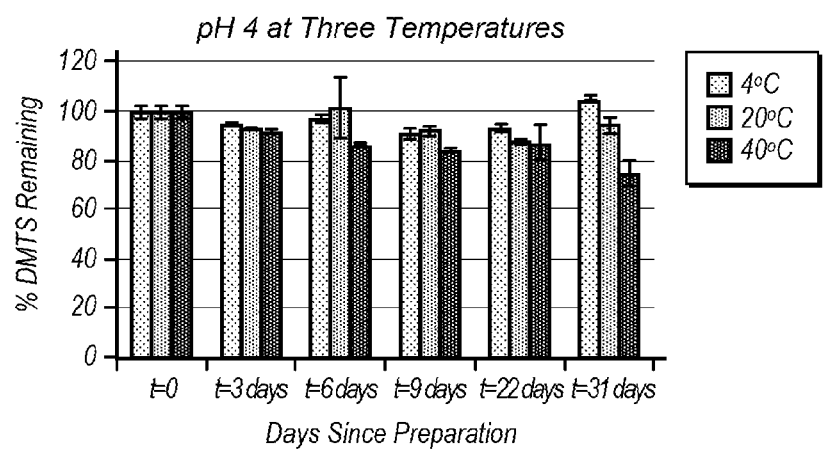
Figure 11E:
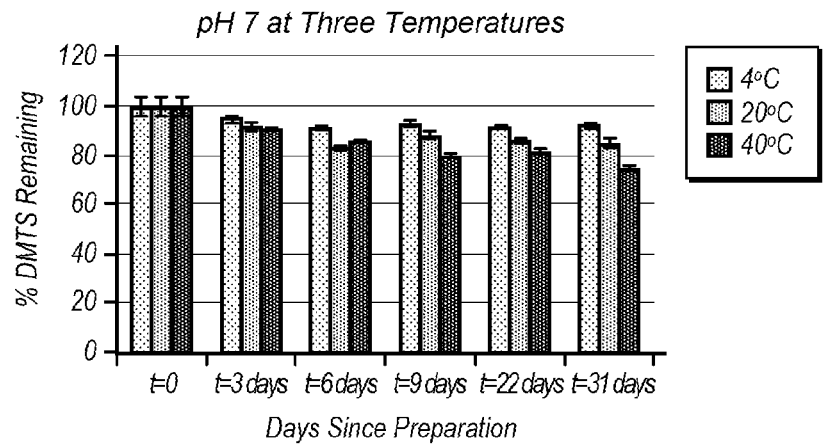
Figure 11F:
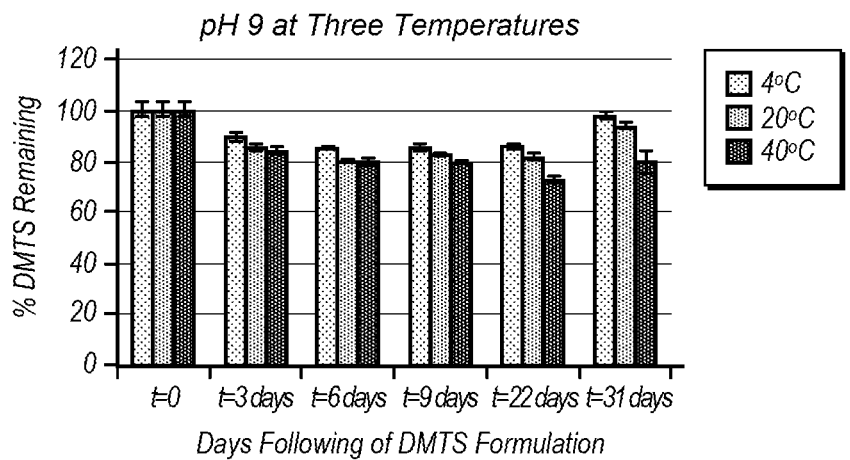
Figure 11G:
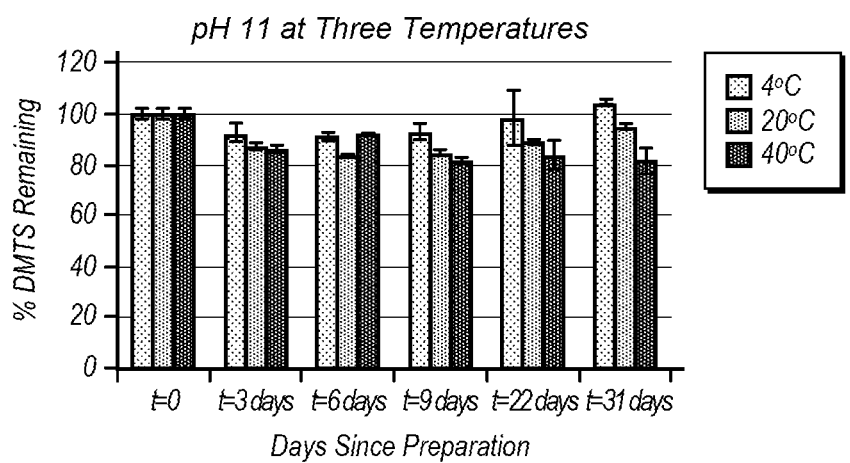

Injection volume optimization—With intramuscular injection, it is important to keep the injection volume minimized. It was experimentally proven, that the higher the Polysorbate 80 concentration in the formulation, the higher DMTS concentration can be achieved (FIG. 5). It is not recommended to exceed the 20% Polysorbate 80 concentration: There was no additional advantages with the 20% Polysorbate 80 vs. the 15% Polysorbate 80 in the in vivo efficacy studies (Table 3) nor in the stability studies. (FIG. 11A, 11B).

Storage stability—Stability studies have been performed as a function of temperature, pH, light and type of sealing of the container. FIGS. 11C-11G show the temperature effects at pH=2, 4, 7, 9 and 11. Samples prepared at pH=7, stored in refrigerator (+40 C) showed optimal stability (98%) out to 31 days. (No data yet beyond 31 days). It was also shown, that the double sealed storage method helped to prevent evaporation/oxidation. There was not any oxidation product detected in the samples analyzed by HPLC and GC-MS over one month.

Residence time—Experiments showed a half-life of about 30 mins. This is considered a sufficient half-life for cyanide toxicity antidotes. (FIG. 9)

Figure 10A:
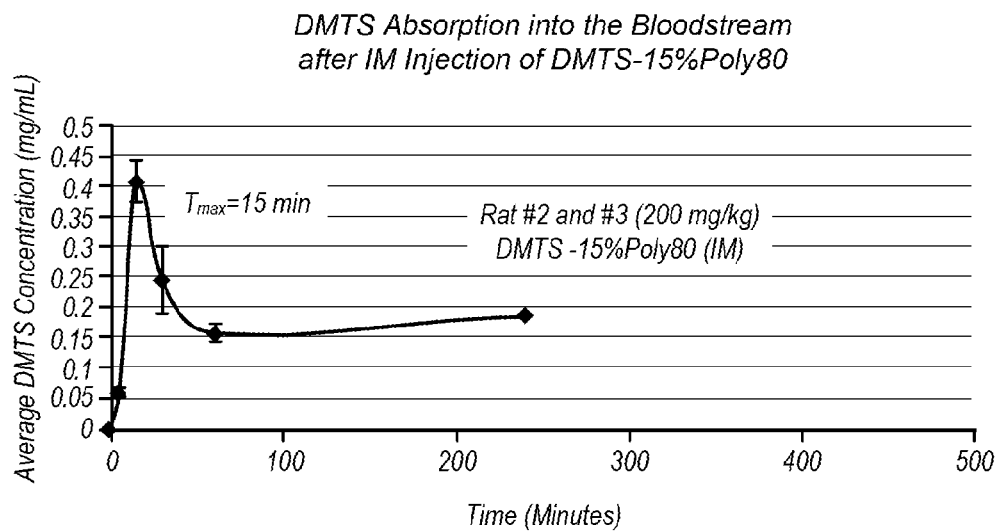
FIGS. 10 A-B depict absorption kinetical data obtained by injecting DMTS dissolved in a solvent system composed of 15% Poly80 in water into rats at the doses of 200 mg/kg and 100 mg/kg.
Figure 10B:
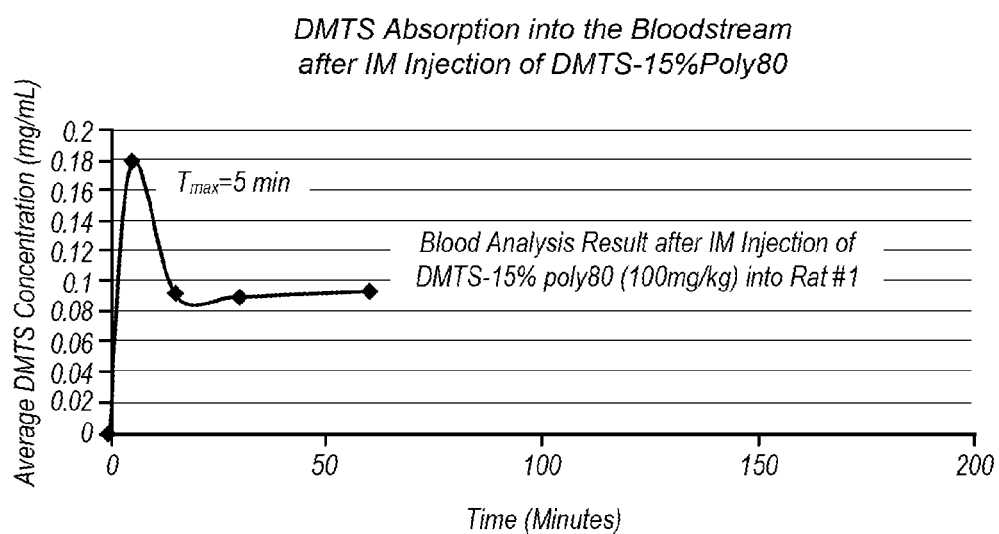

Rapid absorption—Experiments showed a relatively fast absorption. The maximum concentration was achieved in about 5 mins (at 100 mg/kg dose) and about 15 mins (at about 200 mg/kg dose). The disappearance of the DMTS from blood is a result of: a) elimination and b) distribution to organs. Similar conclusion can be drawn for the residence time experiments. As a highly lipid soluble molecule, it is expectable that it distributes from the circulation to organs quickly. However, this process does not destroy the "value" of the drug as a therapeutic agent, since CN also distributes to organs quickly. (FIGS. 10A, 10B)

In vivo Efficacy—Previous in vivo antidotal therapy data was determined using a composition composed of 15% Polysorbate 80 in water, with 50 mg/ml DMTS. These data showed that there is no significant difference in the in vivo efficacy between the composition comprising 15% Polysorbate 80+50 mg/ml DMTS vs. 20% Polysorbate 80+50 mg/ml DMTS (data also shown in Table 3). The advantage of the 20% Polysorbate 80 solvent system is that it can dissolve more DMTS (see FIG. 5), therefore the injection volume could be even further reduced if necessary.

In summary: The advantages of the formulations set forth herein are:

1.) The formulations do not cause muscle necrosis vs. neat DMTS
2.) The formulations have good storage stability
3.) The formulations provide rapid absorption and good pharmacokinetic features
4.) The formulations show good in vivo efficacy, that allows the development of intravenous injection kits.

Micellar Encapsulation of DMTS (mDMTS) and In Vitro and In Vivo Efficacy with mDMTS Reagents DMTS was obtained from Sigma-Aldrich (St. Louis, Mo., USA) and was used as the sulfur donor. 1,2-distearoyl-sn-glycero-3-phosphoethanolamine-N-[methoxy(polyethylene glycol)-2000] (ammonium salt) ($PEG_{2000}$-DSPE) was purchased from Avanti Polar Lipids (Alabaster, Ala., USA). D-α-tocopheryl polyethylene glycol 1000 succinate was purchased from Sigma-Aldrich (St. Louis, Mo., USA). Potassium cyanide (KCN) was obtained from VWR International (Suwanee, Ga., USA) and a stock solution in distilled water was prepared and used throughout the experiments. Materials for the CN conversion included KCN, formaldehyde, ferric nitrate reagent, monobasic sodium phosphate monohydrate and dibasic sodium phosphate anhydrous (VWR International, Suwanee, Ga., USA) and rhodanese, type II from bovine liver (Sigma Aldrich, St. Louis, Mo., USA). Acetonitrile of HPLC grade was obtained from Sigma-Aldrich (St. Louis, Mo., USA).

Determination of CN Conversion to SCN

The conversion of CN to thiocyanate (SCN) by DMTS was measured spectrophotometrically (Genesys 10UV, Thermo Electron Corporation, Waltham, Mass.) using the method of Westley with minor modifications. (Westley J. Thiosulfate: cyanide sulfurtransferase (rhodanese), Methods in enzymology 1981; 77: 285) Briefly, 200 µl of various concentrations of DMTS in ethanol, 200 µl of 10 mM phosphate buffered saline, 200 µl of 250 mM KCN and 400 µl of deionized water were mixed. In the case of efficacy testing in the presence of Rh, 5 µl of 1 mg/mL of Rh solution (161 units/ml, one unit of Rh is defined to convert one micromole of CN to SCN per min at pH 8.6, at 25° C.) was added to the mixture at the start of the experiment replacing 5 µl of deionized water. After incubating for five minutes, the reaction was arrested by adding 500 µl of 15% (v/v) formaldehyde and colorized with 1.5 ml of ferric nitrate reagent. The color development was monitored at $OD_{464}$ nm. Tests were performed with concentrations ranging from 25 mM to 0.156 mM with two fold serial dilutions in between and the results are presented at each data point as the average of triplicate assays. Conversion tests in the presence of the micelle forming agent were conducted only at the higher concentrations.

Preparation of Micellar DMTS (mDMTS)

The preparation of micelles and the loading of DMTS to form mDMTS were performed in 5 consecutive steps. To optimize the manufacturing steps a number of variables were tested before the final technology was developed: Step 1: preparation of stock solutions of $PEG_{2000}$-DSPE with and without DMTS in ethanol. Step 2: evaporation of an aliquot of the stock solutions to form a lipid film (water bath temperature 45° C. for 30 minutes followed by room temperature for 10 minutes; rotation speed: level 8; vacuum: 90 mbar; Ar gas pressure: <5 lbs/sec). Step 3: rehydration of lipid film with distilled water to yield concentrations of 1.78 mM, 3.564 mM, 8.91 mM, 17.82 mM and 26.73 mM of $PEG_{2000}$-DSPE. Step 4: addition of excess DMTS where it was not dissolved in the stock solution. Step 5: sonication at 50° C. for 20 minutes or vortexing.

The prepared samples were stored at 2-8° C. for one week in sealed containers to reach equilibrium solubility and to avoid evaporation. DMTS content of the samples was measured using the HPLC-UV method. Following the elaboration of the ideal preparation method micelles comprising $PEG_{2000}$-DSPE/TPGS (molar ratio 1:1) were prepared using the optimized method (step 1 without dissolved DMTS, step 2, step 3, step 4, step 5 with vortexing) and DMTS content was determined.

Micelles used for the animal studies were prepared using the optimized technology. Briefly, a stock solution of $PEG_{2000}$-DSPE was prepared in ethanol and a lipid film was formed by evaporating the organic solvent in a round bottom flask with the help of a rotavap (Buchi Rotavapor R-210 with Vacuum controller v-855 and vacuum pump 700). The lipid film was then placed in a desiccator at room temperature till further use. For encapsulation of the sulfur donor and rehydration of the film, 2 mg/ml of DMTS and distilled water were added to the lipid film followed by vigorous vortexing for 5 minutes. The result was a translucent liquid.

Head-Space Solid Phase Micro-Extraction-Gas Chromatography-Mass Spectrometry (SPME-GC-MS)

A manual SPME holder and fibers coated with polydimethylsiloxane (PDMS, 100 µm film thickness) were purchased from Sigma-Aldrich (St. Louis, Mo., USA). Equivalent volumes of mDMTS and DMTS in alcohol as a solvent were incubated in GC vials at 37° C. for 0, 0.5, 2, 4 and 8 h. At the end of specified incubation time, the SPME fiber was exposed to the head space of the vial for 5 min to extract DMTS. After SPME, DMTS was thermally desorbed at the GC injection port and analyzed by a FOCUS GC coupled to a DSQ II mass spectrometer (Thermo Scientific, West Palm Beach, Fla., USA). A DB-5 ((5%-phenyl)-methyl-polysiloxane) capillary column (30 m×0.25 mm i.d., 0.25 µm film thickness) was used throughout the entire experiment. Helium (99.999%) was employed as carrier gas at a constant flow rate of 1.2 mL/min. Chromatographic separations were carried out at the initial temperature held at 40° C. for two minutes, then the temperature was ramped at 30° C. per minute to a final temperature of 200° C., held for 2 minutes. The injection was achieved by inserting SPME fiber in the injection port for 2 minutes under the splitless injection mode. Temperatures of the injection port and the interface of MS detector were set at 250° C. and 280° C., respectively. Electron impact (EI) was used as the ionization source.

Animals

Therapeutic In Vivo Experiments with mDMTS Formulations

For therapeutic experiments, mDMTS (12.5 mg/kg) was administered intramuscularly after CN exposure. CN was injected subcutaneously in all experiments. LD50 values were determined by the Dixon up and down method (simulated up and down study) and the estimated 95% confidence interval was determined by the method of Bruce ((Bruce R. D. 1985. An Up-and-Down procedure for acute toxicity testing. Fundam Appl Toxicol. 5:15-157). In detail, mDMTS was injected intramuscularly into the rear right leg of the mouse 30 seconds after the injection of an initial dose of KCN. The mice were then inspected if they stayed alive or died, and the same procedure was repeated with a higher or a lower dose of KCN. This pattern was followed until the stopping conditions were met (determined by the computer software program, "Implementation of Dixon & Massey UDP, Introduction to Statistical Analysis", 1983, pp. 434-438), meaning that enough data were collected to determine the LD50 values. 10 animals were used for the LD50 determination. Injection volumes of KCN solution and mDMTS ranged from 84 to 162 µl and 144 to 197 respectively. The following formula was used for the calculation of the antidote potency ratio (APR): APR=LD50 of CN with the antidote(s)/LD50 of CN without antidote(s) (control).

Histopathology of Mouse Tissue after Intramuscular Injection of mDMTS:

Mice were injected with 50, 100 and 150 µl of mDMTS intramuscularly in the caudal femoral region. Animals were sacrificed at 4, 8, 12, and 24 h post treatment and the legs were collected in 10% formalin. For histopathological studies, the tissues were trimmed, embedded in paraffin, sectioned at 4 µm and adhered to slides, routinely processed, and stained with hematoxylin and eosin.

CN Conversion Efficiency of DMTS Vs. TS

Figure 12:
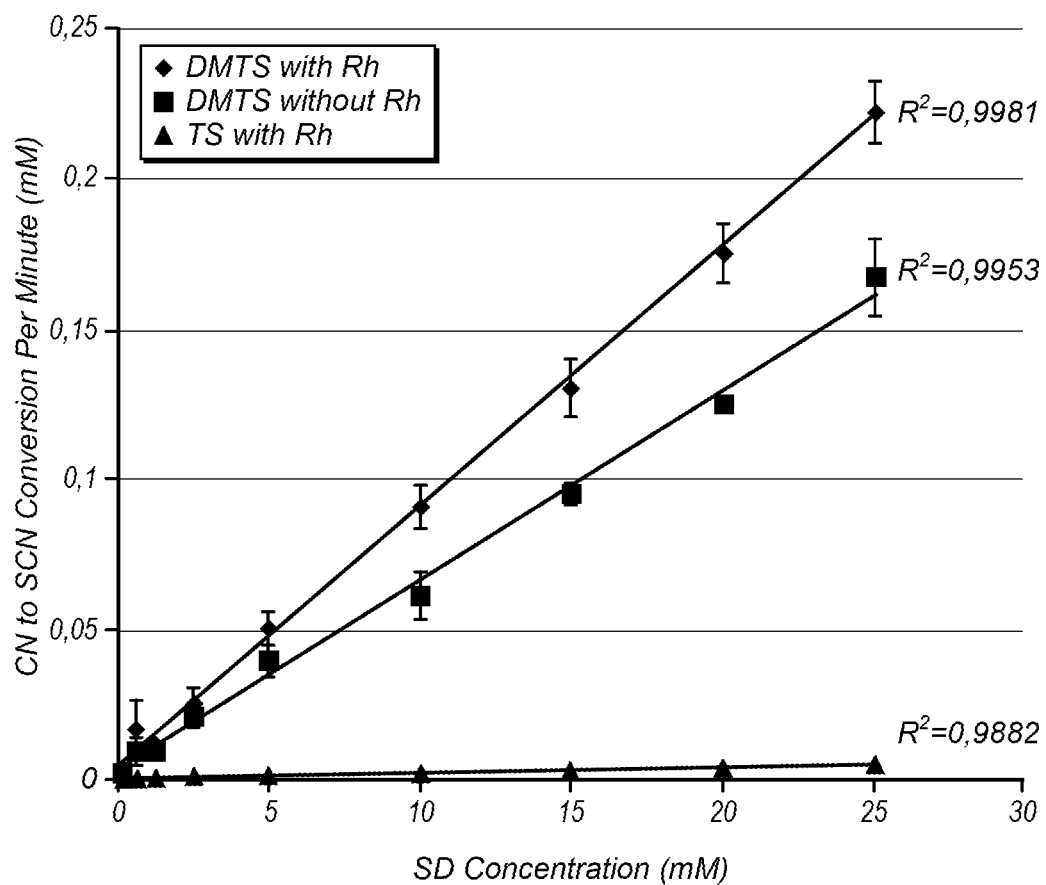
FIG. 12 depicts CN conversion efficiency of DMTS vs. TS in the presence and in the absence of Rh as a function of SD concentration.

The rate of SCN formation from CN in the presence of a sulfur donor reveals the in vitro sulfur donor efficacy of the tested molecule. Results detailed in FIG. 12, describing the efficacy of TS in the presence of Rh indicate that the conversion efficiency of TS is low. It was previously shown that the conversion efficiency of TS in the absence of Rh is also very low and can be characterized with the equation of $8 \times 10^{-5}x + 0.0011$. In the case of TS with Rh the equation is $0.0002x + 0.0013$, indicating the very pronounced effect of Rh in the conversion efficiency of TS. The CN to SCN conversion rate of DMTS with and without Rh clearly indicates the much superior efficacy of DMTS, both in the presence and absence of Rh to that of TS. The slope of the two curves gives a ratio of 0.0086/0.0063 in favor of DMTS in the presence of Rh showing the Rh dependency of the antidote. These studies clearly underline the in vitro efficacy of DMTS as a CN antidote, thus preparation of a pharmaceutically acceptable composition was initiated.

In order to rule out the possible unfavorable interaction—that would possibly inhibit the SCN conversion efficiency—between the antidote molecule and the applied excipient $PEG_{2000}$-DSPE, further in vitro tests were employed. Results showed that DMTS in the presence of $PEG_{2000}$-DSPE efficiently converts CN to SCN, and the conversion rate is very similar to the results obtained with DMTS in the absence of $PEG_{2000}$-DSPE. Additionally, the conversion rate of the excipient by itself is zero upto a concentration of 50 mg/ml (data not shown). The data prove that the in vitro antidotal efficiency of DMTS is not hampered by the use of the applied excipient; furthermore, the excipient by itself does not play a role in the conversion. Overall it can be concluded that the SCN formation is favorable without the $PEG_{2000}$-DSPE at both concentrations and the micelle forming agent is inert in respect of CN detoxification, therefore its use in vivo is recommended.

Optimization of Micelle Preparation Technology

DMTS exhibits very poor water solubility thus an appropriate vehicle, namely a micelle composition had to be developed for the in vivo studies. Prior to solubilizing DMTS in the micelles, its preparation technology was optimized dividing the process into 5 steps as described above.

An important finding of the optimization studies was that that DMTS should not be added to the stock solution containing $PEG_{2000}$-DSPE in ethanol but should be added to the micelles following hydration. This technological step is crucial because as DMTS assays following the micelle preparation showed only a very low concentration of antidote was present in the micelle solution when DMTS was added to the initial solution. This phenomenon can be linked the enhanced evaporation/degradation of DMTS during the film formation step of the preparation. A second, equally important discovery was made during the optimization, namely that sonication at 50° C. for 20 minutes also contributes to loss of DMTS; therefore, this manufacturing step should not be applied. Based on these findings an optimized technology is presented for the manufacture of micelles loaded with a liquid drug subject to evaporation/degradation on heating. The optimized micelle formation is described above.

DMTS Loaded Micelle Preparation, and CN Conversion by mDMTS

Figure 13:
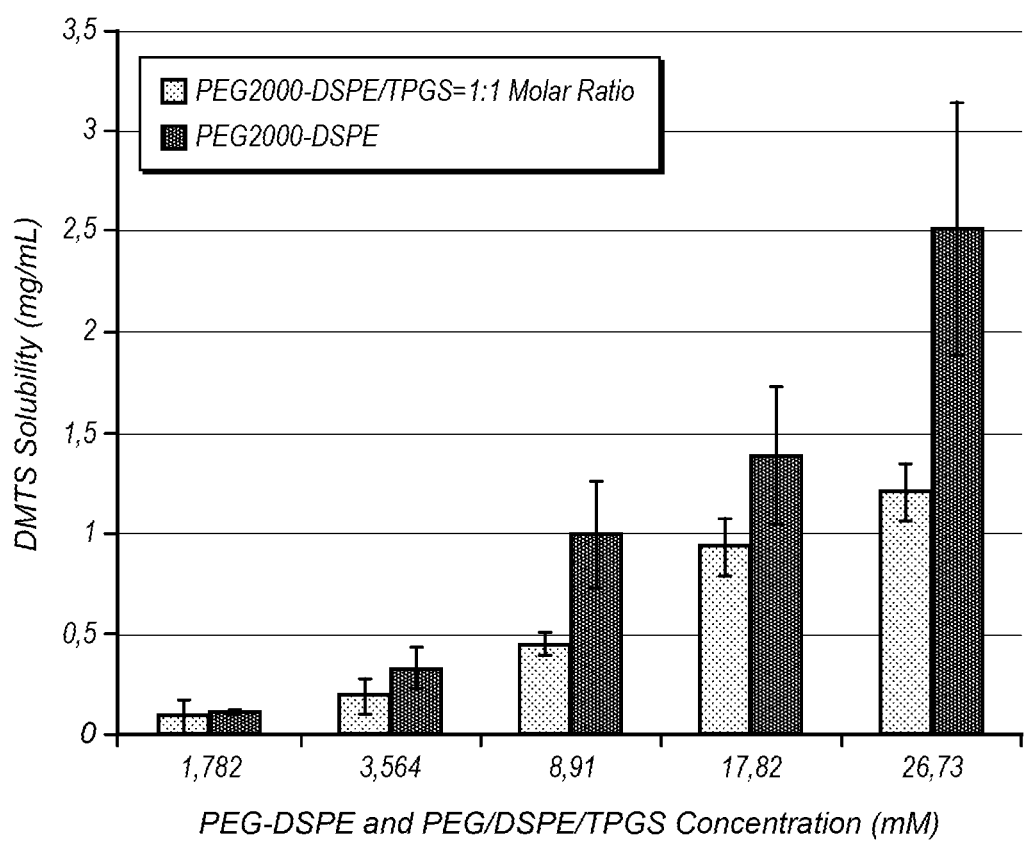
FIG. 13 depicts the solubility of DMTS in $PEG_{2000}$-DSPE micelles and mixed micelles comprising PEGnoo-DSPE/TPGS (molar ratio 1:1)

Applying the optimized technology $PEG_{2000}$-DSPE and mixed micelles comprising $PEG_{2000}$-DSPE/TPGS (molar ratio 1:1) were prepared and maximum DMTS solubility was determined in all the samples (FIG. 13). It was revealed that 1) as the concentration of the micelles increased so did the concentration of solubilized DMTS, 2) $PEG_{2000}$-DSPE exhibited a superior solubility enhancing effect compared to the mixed micelles at all examined concentrations. Highest solubility was seen at 26.73 mM $PEG_{2000}$-DSPE concentration where a maximum DMTS solubility of 2.5 mg/ml was reached. Although further solubility enhancement was expected at higher micelle forming agent concentration, due to the high cost of these excipients this would not be advantageous.

Investigating mDMTS by SPME-GC-MS

Figure 14:
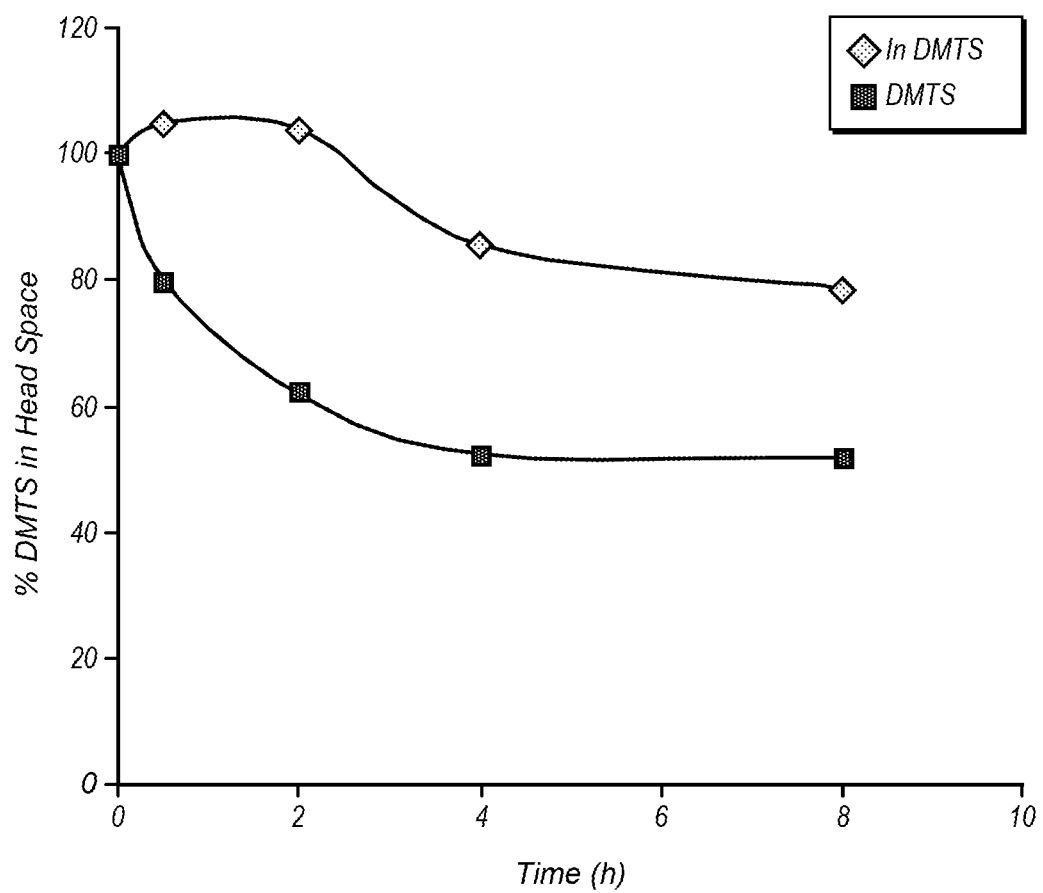
FIG. 14 depicts the volatility of micellar DMTS (mD-MTS) and DMTS in ethanol incubated at 37° C.

During manufacturing processes it was noted that DMTS might volatilize. It was considered that alongside the beneficial solubility enhancing effect of the micelles they migth also decrease the rate of volitalization. As demonstrated in FIG. 14, the micelles were efficient in stabilizing the volatile DMTS (boiling point −58° C.) and proved to hinder the volatilization of DMTS better than plain DMTS in alcohol when incubated at 37° C. The amount of DMTS in the head space remains constant for almost two hours in the case of mDMTS whereas with DMTS in alcohol it rapidly declines and after eight hours has declined to about 60% of the original levels. Further test have to be performed to determine the long term stability of the preparation.

Therapeutic In Vivo Experiments with DMTS Formulations

Based on the solubility studies, a preparation of 26.73 mM $PEG_{2000}$-DSPE+2 mg/ml of DMTS was selected for in vivo testing. Results proved that DMTS is an effective antidote in antagonizing CN intoxication, since an antidotal protection of 2×LD50 was seen at the low dose dose of 12.5 mg/kg (Table 4). It is believed that similarly to the in vitro result, the in vivo efficacy would increase with the applied dose, but the present formulation would not allow for a higher dose because the injection volume would not be tolerated by the mice. Comparing the efficacy of DMTS with that of earlier tests performed with TS and methyl propyl trisulfide when TS at doses of 100 mg/kg and 200 mg/kg provided APRs of 1.1 and 1.25 respectively, and methyl propyl trisulfide at doses of 100 mg/kg and 200 mg/kg provided APRs of 1.2 and 1.67 respectively it can be concluded, that DMTS is significantly more effective than both investigated sulfur donors, because a higher APR of 2 was reached at a much lower dose of 12.5 mg/kg. These test also proved that the intramuscular route of administration is effective in case of mDMTS, because the effect of the antidote was immediately showing that the absorption of the antidote candidate is rapid enough to counteract the fast acting CN.

TABLE 4

Therapeutic LD50 and APR value for mDMTS

| Composition | DMTS dose (mg/kg) (im) | CN LD50 (control) mg/kg (sc) | CN LD50 in the presence of DMTS | APR |
| --- | --- | --- | --- | --- |
| 2.5 mg/mL DMTS in 26.75 mg/mL $PEG_{2000}$-DSPE | 12.5 | 8.15 (6.59-10.08) | 17.09 (13.97-20.92) | 2.09 |

Histopathology of Mouse Tissue after Intramuscular Injection of mDMTS

The three DMTS treatments were similar across dosages and were similar across time points. Time points demonstrated an initial change (4 h) of muscle swelling, degeneration, and fragmentation accompanied by very mild edema and fibrin and neutrophil infiltration. By 8 h macrophages were observed as part of the inflammatory cell infiltrate. By 12 and 24 hours the edema and inflammation had increased to some degree and there was evidence of satellite cell hyperplasia at the periphery of some degenerating fibers (initial attempts at regeneration). The untreated (negative) control had no significant lesions within the muscle. The treated (positive) control of 10 mM phosphate buffer had acute degenerative and inflammatory lesions similar to those observed with each treatment at the 8-hour time point. All changes were interpreted to be most likely due to trauma/pressure associated with an intramuscular injection, and not toxic effects of the material injected.

CONCLUSION

To overcome the deficiency of the presently available CN antidotes of Nithiodote and Cyanokit, (intravenous administration, methemoglobinemia by sodium nitrite, pour sulfur donor efficiency and pour cell penetration capability and high Rh dependency of thiosulfate), a series of organo-sulfur molecules have been tested as sulfur donors. Some of them proved to be superior to the present therapy of thiosulfate (more efficient sulfur donor reactivity and higher lipohilicity), and the choice was given to DMTS for further investigations. DMTS proved to be a significantly more efficient sulfur donor than the present therapy of sodium thiosulfate, and it reacts efficiently with CN even without Rh, therefore it seems to be an appropriate candidate for developing an intramuscular injection kit, usable for a mass casualty scenario. Furthermore, DMTS is a known, naturally occurring molecule: it is present in garlic, and used in food industry as flavor enhancer, therefore it seems to be a safe candidate molecule.

These studies are the first to prove that DMTS is efficacious after intramuscular administration. This is an important finding because it shows that a future antidote kit could be formulated as intramuscular product. This would have numerous advantages, such as self-administration, easier handling and distribution in a mass casualty scenario over the currently approved kits which can only be administered intravenously. The use of micelles, proposed in this paper does not fully solve the solubility issues of DMTS, but is a valuable initial step in reaching an adequate formulation. The advantages of mDMTS vs. un-encapsulated DMTS are 1) elimination of muscle necrosis, 2) the rate of evaporation within mDMTS is suppressed, that can provide a level of stability for the formulation. Two types of micelles ($PEG_{2000}$-DSPE and $PEG_{2000}$-DSPE/TPGS) were prepared and tested for their ability to encapsulate DMTS. The method of micelle preparation for the liquid drug, DMTS was optimized and it was demonstrated that the $PEG_{2000}$-DSPE preparation can dissolve up to 2.5 mg/ml of the antidote candidate. However, keeping it in consideration that the injection volume has to be kept minimized, with this mDMTS a maximum dose of 12.5 mg/kg DMTS can be applied. However, even this low dose of DMTS showed a remarkable in vivo therapeutic efficacy of 2×$LD_{50}$ protection in a mice model. When DMTS load of higher than 2.5 mg/ml was applied to the micelle forming excipients, a mixture of micelles and emulsions were seen, that gave higher in vivo efficacy, but due to the lack of the physical stability of the composition and standardized process parameters the formulation could not be further tested (Petrikovics unpublished data). For applying standardized higher DMTS dose, further development of advanced formulations is necessary.

DMTS Formulations

Preparation of 15% (m/m) Polysorbate 80

1.2 g of polysorbate 80 was measured and combined with 6.8 g of distilled water to create 8 g of 15% polysorbate 80 solutions. The solution vigorously vortex for about 5 minutes until all of the polysorbate 80 was dissolved.

Preparation of 50 mg/mL DMTS in 15% Poly80

5 mL of 50 mg/mL DMTS in 15% polysorbate 80 was generated in the following way: 0.25 g (250 mg) of DMTS was weighed into a 5 mL volumetric flask, and filled to the mark with the 15% polysorbate 80 solution. The flask was capped and then vigorously vortexed until the DMTS was completely dissolved. This can take a long time (20-30 minutes). The results should be a solution where there is no sign of any oil drops or any sort of sedimentation at the bottom.

Increased Quantity—DMTS Formulation with 15% Polysorbate 80

15% Poly80 Preparation

Add 15.00 g poly 80 in VWR flask; add D.I. water to the flask until 100.00 g; Hand shake for 30 mins (the poly 80 should be totally dissolved); Put the solution in the refrigerator overnight.

50 mg/Ml DMTS in 15% Poly80

Take the pre-prepared 15% poly 80 out of the refrigerator before use. (Around 30 mins in room temperature); Add 1.2502 g DMTS in 25 ml volumetric flask; Add the prepared 15% poly 80 from above until the marked line; Hand vortex 45 mins then transfer the solution to the 25 ml cramped vial; Shake another 30 mins then keep in the refrigerator for overnight; Take the solution out of the refrigerator and shake 10 mins before use.

Formulations for DMTS+TS and or SN Combinations

For Combination Studies with DMTS+TS and or SN, the components were formulated in 15% Poly80. (Table 5). The combination formulations were tested including DMTS+ sodium thiosulfate (TS) and DMTS and sodium nitrite. Results are presented in Table 5.

TABLE 5

APR results for various combination therapies

| Antidotes | Treatments/Doses of Antidotes (im) | Formulation composition | APR* |
|---|---|---|---|
| DMTS | DMTS (12.5 mg/kg) | DMTS (2.5 mg/ml in 26.75 mg/ml $PEG_{2000}$-DSPE) (micelles) | 2.1 |
| DMTS | DMTS (25 mg/kg) | DMTS (50 mg/ml) in 15% Poly80 | 1.7 |
| DMTS | DMTS (50 mg/kg) | DMTS (50 mg/ml) in 15% Poly80 | 2.0 |
| DMTS | DMTS (100 mg/kg) | DMTS (50 mg/ml) in 15% Poly80 | 3.4 |
| DMTS | DMTS (200 mg/kg) | DMTS (50 mg/ml) in 15% Poly80 | 4.1 |
| DMTS | DMTS (100 mg/kg) | DMTS (50 mg/ml) in 20% Poly80 | 3.2 |
| TS | TS (100 mg/kg) (im) | TS (50 mg/ml in PBS, pH = 7.0) | 1.1 |
| TS | TS (200 mg/kg) (im) | TS (50 mg/ml in PBS, pH = 7.0) | 1.3 |
| DMTS + TS | DMTS (25 mg/kg) + TS (200 mg/kg) (im) | DMTS (50 mg/ml) in 15% Poly80 TS (100 mg/ml) in 15% Poly80 (separate legs) | 2.1 |
| DMTS + TS | DMTS (50 mg/kg) + TS (200 mg/kg) | DMTS (50 mg/ml) in 15% Poly80 TS (100 mg/ml) in 15% Poly80 (separate legs) | 2.8 |
| DMTS + TS | DMTS (100 mg/kg) + TS (200 mg/kg) | DMTS (50 mg/ml) in 15% Poly80 TS (100 mg/ml) in 15% Poly80 (separate legs | 4.6 |
| SN | SN (3.2 mg/kg) (im) | SN (10 mg/ml) in 15% Poly80 | 1.0 |
| SN | SN (6.4 mg/kg) (im) | SN (10 mg/ml) in 15% Poly80 | 1.3 |
| DMTS + SN | DMTS (50 mg/kg) + SN (3.2 mg/kg) | DMTS (50 mg/ml) in 15% Poly80 + SN (10 mg/ml) in 15% Poly80 (separate legs) | 2.1 |
| DMTS + SN | DMTS (50 mg/kg) + SN (6.4 mg/kg) | DMTS (50 mg/ml) in 15% Poly80 + SN (10 mg/ml) in 15% Poly80 (separate legs) | 2.9 |
| DMTS + TS + SN | DMTS (25 mg/kg) TS (200 mg/kg) SN (6.4 mg/kg) | DMTS (50 mg/ml) in 15% Poly80 + TS (100 mg/ml) in 15% Poly80 SN (10 mg/ml) in 15% Poly80 | 2.6 |
| DMTS + TS + SN | DMTS (50 mg/kg) TS (200 mg/kg) SN (6.4 mg/kg) | DMTS (50 mg/ml) in 15% Poly80 + TS (100 mg/ml) in 15% Poly80 SN (10 mg/ml) in 15% Poly80 | 2.8 |

In this patent, certain U.S. patents and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A pharmaceutical composition for treating cyanide intoxication in a subject, comprising:
    dimethyl trisulfide dissolved in an aqueous solvent system, wherein the aqueous solvent system comprises: water and a non-ionic surfactant, wherein the concentration of non-ionic surfactant in water is about 5% to about 20% by weight;
    wherein the concentration of dimethyl trisulfide in the aqueous solvent system ranges from about 10 mg/mL to about 100 mg/mL.

2. The pharmaceutical composition of claim 1, wherein the non-ionic surfactant is an ethoxylated castor oil.

3. The pharmaceutical composition of claim 1, wherein the non-ionic surfactant is a polysorbate.

4. The pharmaceutical composition of claim 1, further comprising one or more additional compounds, wherein the additional compounds are capable of removing and/or detoxifying cyanide in a subject.

5. The pharmaceutical composition of claim 1, wherein the pharmaceutical composition further comprises sodium thiosulfate.

6. The pharmaceutical composition of claim 1, wherein the pharmaceutical composition further comprises sodium nitrite.

7. A method of treating cyanide intoxication in a subject, comprising:
   administrating to a subject who would benefit from such treatment a therapeutically effective amount of a pharmaceutical composition, the pharmaceutical composition comprising;
   dimethyl trisulfide dissolved in an aqueous solvent system, wherein the aqueous solvent system comprises: water and a non-ionic surfactant, wherein the concentration of non-ionic surfactant in water is about 5% to about 20% by weight;
   wherein the concentration of dimethyl trisulfide in the aqueous solvent system ranges from about 10 mg/mL to about 100 mg/mL.

8. The method of claim 7, wherein the dimethyl trisulfide solution is administered as a solution intramuscularly.

9. The method of claim 7, wherein the dimethyl trisulfide solution is administered as a solution subcutaneously.

* * * * *

UNITED STATES PATENT AND TRADEMARK OFFICE
CERTIFICATE OF CORRECTION

| | |
|---|---|
| PATENT NO. | : 9,456,996 B2 |
| APPLICATION NO. | : 14/685014 |
| DATED | : October 4, 2016 |
| INVENTOR(S) | : Petrikovics et al. |

It is certified that error appears in the above-identified patent and that said Letters Patent is hereby corrected as shown below:

In the Specification

Column 1 Line 4:

Please add the following paragraph before the section entitled "Priority Claim":

STATEMENT REGARDING FEDERALLY SPONSORED RESEARCH OR DEVELOPMENT

This invention was made with government support under award no. W81XWH-12-2-0126 awarded by the United States Army Medical Research and Materiel Command. The government has certain rights in the invention.

Signed and Sealed this
Eighteenth Day of July, 2017

Joseph Matal
*Performing the Functions and Duties of the
Under Secretary of Commerce for Intellectual Property and
Director of the United States Patent and Trademark Office*